United States Patent
Murata (12)

(10) Patent No.: US 6,281,412 B1
(45) Date of Patent: Aug. 28, 2001

(54) METHOD FOR CREATING OSMOTIC-PRESSURE-TOLERANT PLANT

(75) Inventor: Norio Murata, Aichi-ken (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 08/930,001

(22) PCT Filed: Mar. 27, 1996

(86) PCT No.: PCT/JP96/00797

§ 371 Date: Sep. 26, 1997

§ 102(e) Date: Sep. 26, 1997

(87) PCT Pub. No.: WO96/29857

PCT Pub. Date: Oct. 3, 1996

(30) Foreign Application Priority Data

Mar. 27, 1995 (JP) ..................................... 7-106819

(51) Int. Cl.$^7$ ........................... C12N 15/82; C12N 15/74; C12N 5/00; C12N 5/04
(52) U.S. Cl. ........................... 800/288; 435/468; 435/741; 435/410; 435/419; 435/252.1; 435/252.3; 800/290; 800/295; 800/298; 800/289; 800/320.2; 800/306; 800/320
(58) Field of Search ................................ 435/418, 252.3, 435/468, 252.1, 471, 410, 419; 800/205, 255, DIG. 57, 235, DIG. 16, 288, 289, 290, 320.02, 295, 298, 317.3, 320, 306; 536/23.14

(56) References Cited

FOREIGN PATENT DOCUMENTS

97/24026  7/1997 (WO).

OTHER PUBLICATIONS

Rathinasabapathi, B. et al., Metabolic Engineering of Glycine Betaine Synthesis: Plant Betaine Aldehyde Dehydrogenases Lacking Typical Transit Peptides are Argeted to Tobacco Chloroplasts where they confer Betaine Aldehyde Resistance. vol. 193, 1994, pp. 155–162.
P. Deshnium et al., A. globiformis codA gene. Feb. 27, 1995 (EMBL Accession No. X84895).
Mark A. Mackay et al., Organic osmoregulatory solutes in cyanobacteria. Chemical Abstracs, vol. 101, No. 25, Dec. 17, 1984.
Holmstoem, K. –O et al., Production of the 1–3, 5–10 *Escherichia Coli* Betaine–Aldehyde Dehydrogenase, An Enzyme required for the Synthesis of the Osmoprotectant Glycine Betaine, In Transgenic Plants. vol. 6, No. 5, 1994, pp. 749–758.
Reed, R.H. et al., The Responses of Cyanobacteria to Salt Stress, vol. 28, Apr. 1987.
Rathinasabapathi, B. et al., Cultivated And Wild Rices Do Not Accumulate Glycinebetaine Due to Deficiencies in Two Biosynthetic Steps. vol. 33, May 1993, pp. 534–538.

Saneoka, H. et al., Salt Tolerance of Glycinebetaine–Deficient and –Containing Maize Lines, vol. 107, Feb. 1995, pp. 631–638.
McCue, K. et al., Drought and Salt Tolerance: Towards Understanding and Application. vol. 8, Dec. 1990, pp. 358–362.
Pilon–Smits, E.A.H., et al., Improved performancepf trnasgenice fructan–accumulating tobacco under drought stress, vol. 107, Jan. 1995, pp. 125–130.
Tarczynki, M. C. et al., Stress Protection of Transgenic Tobacco by Production of the Osmolyte Mannitol. vol. 259, Jan. 22, 1993, pp. 508–510.
Deshnium et al. Plant Molecular Biology. 1995. vol. 29: 897–907.*
Roche et al. Plant Molecular Biology. 1993. vol. 22: 971–983.*
Wan and Lemaux. Plant Physiol. 1994. vol. 104: 37–48.*
Zaghmout and Torello. J. of Plant Physiol. 1992. vol. 140: 101–105.*
Valvekens et al. Proc. Natl. Acad. Sci. 1988. vol. 85: 5536–5540.*
Rozwadowski et al. Journal of Bacteriology. 1991. vol. 173: 472–478.*
Ausubel et al. Short Protocols in Molecular Biology. John Wiley & Sons. 1989.*
Chan et al. Plant Molecular Biology. 1993. vol. 22: 491–506.*
Patcharaporn et al., Plant Molecular Biology, vol. 29, pp. 897–907 (1995).
Nomura et al., Plant Physiol., vol. 107, pp. 703–708 (1995).
Rozwadowski et al., Journal of Bacteriology, vol. 173 No. 2, pp. 472–478 (1991).
Rohdes et al., Annu. Rev. Plant Physiol. Plant Mol. Biol., vol. 44, pp. 357–384 (1993).

* cited by examiner

*Primary Examiner*—David T. Fox
*Assistant Examiner*—Ousama M-Faiz Zaghmout
(74) *Attorney, Agent, or Firm*—Birch, Stewart, Kolasch & Birch, LLP

(57) ABSTRACT

A method for producing salt-tolerant and/or osmotolerant plants, which comprises the step of transforming a plant with a recombinant vector carrying a gene encoding choline oxidase, as well as the salt-tolerant and/or osmotolerant plants produced by said method or a progeny thereof having the same properties.

9 Claims, 14 Drawing Sheets

FIG. II
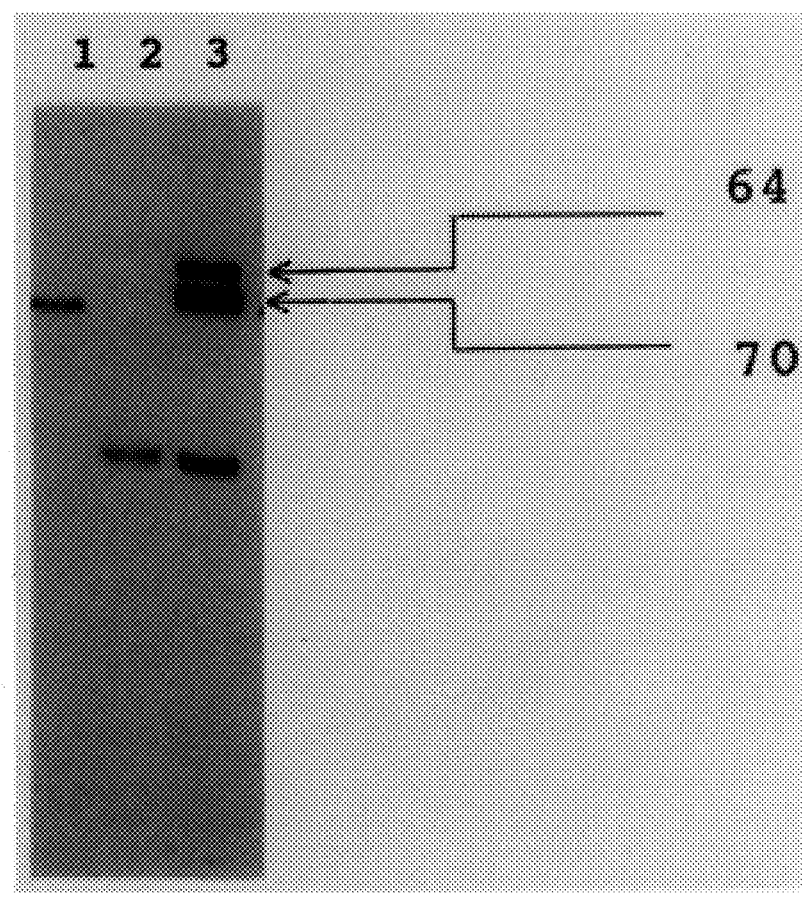

FIG. 13
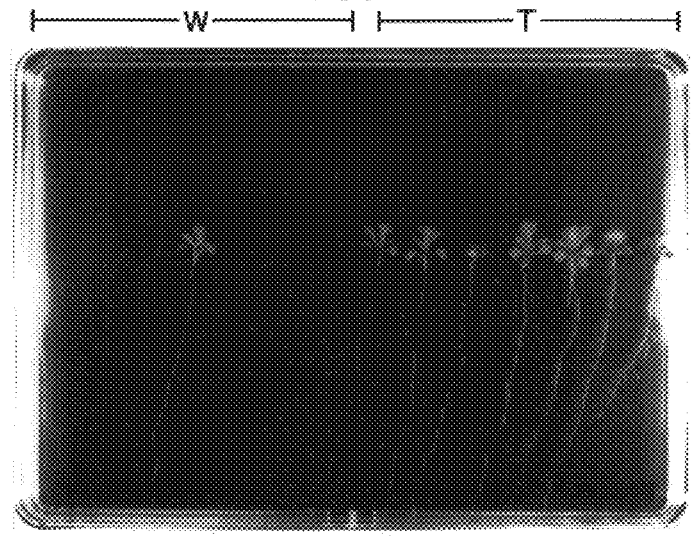
100mM
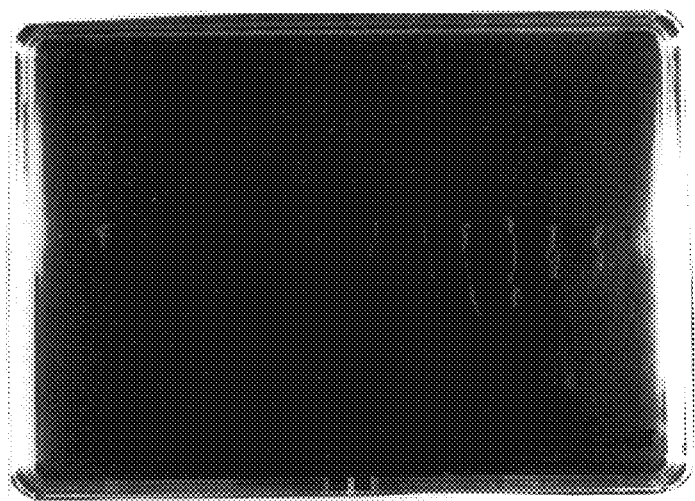
200mM
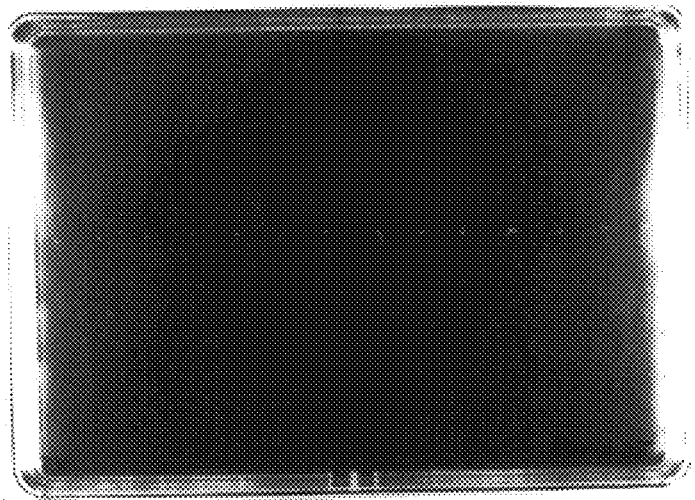
300mM

SEQUENCE LISTING

<160> NUMBER OF SEQ ID NOS: 8

<210> SEQ ID NO 1
<211> LENGTH: 2400
<212> TYPE: DNA
<213> ORGANISM: Arthrobacter globiformis
<220> FEATURE:
<221> NAME/KEY: CDS
<222> LOCATION: (361)..(2001)

<400> SEQUENCE: 1

```
gggaatatcc gtcgtcgtag acgagcccct cggcccgtgt aaagtggag accttccaca      60 ccgaggacga ggccgtcgcg accgccaacg acaccaacta cgggctgtcc ggcgcggtcc    120
tggacccagg acgccggcaa gacgcagcgc gtggccggcc ggctgcgaca cggcaccgtc    180
tggatcaacg acttccaccc ctacctccca cagaccgagt ggggcggctt cggccagtcc    240
ggcgtcggcc gcgaactcgg cccgaccggc ctggccgagt accaggaggc caagcacatc    300
taccagaaca ccagcccgca gtcaccggc tggttcgctg accacggcaa ggagaactag    360
```

| atg | cac | atc | gac | aac | atc | gag | aac | ctg | agc | gac | agg | gag | ttc | gac | tac | 408 |
|-----|-----|-----|-----|-----|-----|-----|-----|-----|-----|-----|-----|-----|-----|-----|-----|-----|
| Met | His | Ile | Asp | Asn | Ile | Glu | Asn | Leu | Ser | Asp | Arg | Glu | Phe | Asp | Tyr | |
| 1 | | | | 5 | | | | | 10 | | | | | 15 | | |

| atc | gtc | gtc | ggc | ggc | ggg | tcc | gcc | ggg | gcc | gcc | gtc | gcc | gcc | cgg | ctg | 456 |
|-----|-----|-----|-----|-----|-----|-----|-----|-----|-----|-----|-----|-----|-----|-----|-----|-----|
| Ile | Val | Val | Gly | Gly | Gly | Ser | Ala | Gly | Ala | Ala | Val | Ala | Ala | Arg | Leu | |
| | | | 20 | | | | | 25 | | | | | 30 | | | |

| agc | gag | gat | ccc | gca | gtg | agc | gtg | gcg | ctg | gtg | gag | gcc | ggc | ccg | gat | 504 |
|-----|-----|-----|-----|-----|-----|-----|-----|-----|-----|-----|-----|-----|-----|-----|-----|-----|
| Ser | Glu | Asp | Pro | Ala | Val | Ser | Val | Ala | Leu | Val | Glu | Ala | Gly | Pro | Asp | |
| | 35 | | | | | 40 | | | | | 45 | | | | | |

| gac | cgc | ggc | gtg | ccc | gag | gtg | ctg | cag | ctg | gac | cgc | tgg | atg | gag | ctg | 552 |
|-----|-----|-----|-----|-----|-----|-----|-----|-----|-----|-----|-----|-----|-----|-----|-----|-----|
| Asp | Arg | Gly | Val | Pro | Glu | Val | Leu | Gln | Leu | Asp | Arg | Trp | Met | Glu | Leu | |
| 50 | | | | | 55 | | | | | 60 | | | | | | |

| ctg | gaa | tcg | ggc | tac | gac | tgg | gac | tac | ccg | atc | gag | ccg | cag | gag | aac | 600 |
|-----|-----|-----|-----|-----|-----|-----|-----|-----|-----|-----|-----|-----|-----|-----|-----|-----|
| Leu | Glu | Ser | Gly | Tyr | Asp | Trp | Asp | Tyr | Pro | Ile | Glu | Pro | Gln | Glu | Asn | |
| 65 | | | | 70 | | | | | 75 | | | | | 80 | | |

| ggc | aac | tcc | ttc | atg | cgc | cat | gcc | cgt | gcc | aag | gtc | atg | ggc | ggc | tgc | 648 |
|-----|-----|-----|-----|-----|-----|-----|-----|-----|-----|-----|-----|-----|-----|-----|-----|-----|
| Gly | Asn | Ser | Phe | Met | Arg | His | Ala | Arg | Ala | Lys | Val | Met | Gly | Gly | Cys | |
| | | | | 85 | | | | | 90 | | | | | 95 | | |

| tcc | agc | cac | aac | tcc | tgc | atc | gcc | ttc | tgg | gcc | ccg | cgc | gag | gac | ctg | 696 |
|-----|-----|-----|-----|-----|-----|-----|-----|-----|-----|-----|-----|-----|-----|-----|-----|-----|
| Ser | Ser | His | Asn | Ser | Cys | Ile | Ala | Phe | Trp | Ala | Pro | Arg | Glu | Asp | Leu | |
| | | 100 | | | | | 105 | | | | | 110 | | | | |

| gac | gag | tgg | gag | gcc | aag | tac | ggc | gcc | acc | ggc | tgg | aac | gcc | gag | gcg | 744 |
|-----|-----|-----|-----|-----|-----|-----|-----|-----|-----|-----|-----|-----|-----|-----|-----|-----|
| Asp | Glu | Trp | Glu | Ala | Lys | Tyr | Gly | Ala | Thr | Gly | Trp | Asn | Ala | Glu | Ala | |
| | | 115 | | | | | 120 | | | | | 125 | | | | |

| gcc | tgg | ccg | ctg | tac | aag | cgg | ctg | gaa | acc | aac | gag | gac | gcg | ggc | ccg | 792 |
|-----|-----|-----|-----|-----|-----|-----|-----|-----|-----|-----|-----|-----|-----|-----|-----|-----|
| Ala | Trp | Pro | Leu | Tyr | Lys | Arg | Leu | Glu | Thr | Asn | Glu | Asp | Ala | Gly | Pro | |
| | 130 | | | | | 135 | | | | | 140 | | | | | |

| gac | gcg | ccg | cac | cac | ggg | gac | tcc | ggc | ccc | gtg | cac | ctg | atg | aac | gtg | 840 |
|-----|-----|-----|-----|-----|-----|-----|-----|-----|-----|-----|-----|-----|-----|-----|-----|-----|
| Asp | Ala | Pro | His | His | Gly | Asp | Ser | Gly | Pro | Val | His | Leu | Met | Asn | Val | |
| 145 | | | | | 150 | | | | | 155 | | | | | 160 | |

| ccc | ccg | aag | gac | ccg | acc | ggc | gtc | gcg | ctc | ctg | gac | gcc | tgc | gag | cag | 888 |
|-----|-----|-----|-----|-----|-----|-----|-----|-----|-----|-----|-----|-----|-----|-----|-----|-----|
| Pro | Pro | Lys | Asp | Pro | Thr | Gly | Val | Ala | Leu | Leu | Asp | Ala | Cys | Glu | Gln | |
| | | | 165 | | | | | 170 | | | | | 175 | | | |

| gcc | ggc | atc | ccg | cgc | gcg | aag | ttc | aac | acc | ggc | acc | acc | gtg | gtc | aac | 936 |
|-----|-----|-----|-----|-----|-----|-----|-----|-----|-----|-----|-----|-----|-----|-----|-----|-----|
| Ala | Gly | Ile | Pro | Arg | Ala | Lys | Phe | Asn | Thr | Gly | Thr | Thr | Val | Val | Asn | |
| | | 180 | | | | | 185 | | | | | 190 | | | | |

| ggc | gcc | aac | ttc | ttc | cag | atc | aac | cgg | cgc | gcg | gac | ggc | acc | cgc | tcc | 984 |
|-----|-----|-----|-----|-----|-----|-----|-----|-----|-----|-----|-----|-----|-----|-----|-----|-----|
| Gly | Ala | Asn | Phe | Phe | Gln | Ile | Asn | Arg | Arg | Ala | Asp | Gly | Thr | Arg | Ser | |
| | 195 | | | | | 200 | | | | | 205 | | | | | |

-continued

| | | |
|---|---|---|
| tcc agc tcg gtc tcc tac atc cac ccg atc gtc gag cag gag aac ttc<br>Ser Ser Ser Val Ser Tyr Ile His Pro Ile Val Glu Gln Glu Asn Phe<br>210                        215                  220 | 1032 |
| acc ctg cta acc ggc ctg cgc gcc cgc cag ctg gtg ttc gac gcg gac<br>Thr Leu Leu Thr Gly Leu Arg Ala Arg Gln Leu Val Phe Asp Ala Asp<br>225                      230                      235                240 | 1080 |
| agg cgc tgc acc ggc gtc gac atc gtg gac tcc gcc ttc ggc cgc acc<br>Arg Arg Cys Thr Gly Val Asp Ile Val Asp Ser Ala Phe Gly Arg Thr<br>                   245                      250                      255 | 1128 |
| cat cgg ctg acg gcg cgc aat gaa gtc gtg ctc tcc acc ggc gcg atc<br>His Arg Leu Thr Ala Arg Asn Glu Val Val Leu Ser Thr Gly Ala Ile<br>        260                      265                      270 | 1176 |
| gat acg ccg aag ctg ttg atg ctc tcc gga atc ggc ccc gcc gcc cac<br>Asp Thr Pro Lys Leu Leu Met Leu Ser Gly Ile Gly Pro Ala Ala His<br>275                        280                  285 | 1224 |
| ctc gcc gag cac ggc atc gag gtc ctt ggt gga ctc ccc cgg cgt ggg<br>Leu Ala Glu His Gly Ile Glu Val Leu Gly Gly Leu Pro Arg Arg Gly<br>        290                      295                      300 | 1272 |
| cga gca cct gca gga cca ccc gga agg cgt ggt gca gtt cga ggc caa<br>Arg Ala Pro Ala Gly Pro Pro Gly Arg Arg Gly Ala Val Arg Gly Gln<br>305                      310                      315                320 | 1320 |
| gca gcc cat ggt cgc cga gtc cac gca gtg gtg gga gat cgg cat ctt<br>Ala Ala His Gly Arg Arg Val His Ala Val Val Gly Asp Arg His Leu<br>                   325                      330                      335 | 1368 |
| cac ccc cac cga gga cgg cct gga ccg ccc cga cct gat gat gca cta<br>His Pro His Arg Gly Arg Pro Gly Pro Pro Arg Pro Asp Asp Ala Leu<br>                340                      345                      350 | 1416 |
| cgg ctc cgt gcc gtt cga cat gaa cac cct gcg gca cgg cta ccc cac<br>Arg Leu Arg Ala Val Arg His Glu His Pro Ala Ala Arg Leu Pro His<br>355                        360                  365 | 1464 |
| cac gga gaa cgg gct tca gcc tca ccc cga acg tca cgc acg ccc gct<br>His Gly Glu Arg Ala Ser Ala Ser Pro Arg Thr Ser Arg Thr Pro Ala<br>        370                      375                  380 | 1512 |
| ccc gcg gca ctg tcc ggc tgc gca gcc gcg act tcc gcg ata agc cca<br>Pro Ala Ala Leu Ser Gly Cys Ala Ala Ala Thr Ser Ala Ile Ser Pro<br>385                      390                      395                400 | 1560 |
| tgg tcg acc cgc gct act tca ccg acc cag aag ggc cat gac atg cgc<br>Trp Ser Thr Arg Ala Thr Ser Pro Thr Gln Lys Gly His Asp Met Arg<br>                405                      410                      415 | 1608 |
| gtc atg gtc gcc ggc atc cgc aag gcc cgc gaa atc gcc gcc cag ccc<br>Val Met Val Ala Gly Ile Arg Lys Ala Arg Glu Ile Ala Ala Gln Pro<br>                   420                      425                      430 | 1656 |
| gcc atg gcg gaa tgg acc ggc cgc gag ctc tcc ccc ggc gtc gag gcg<br>Ala Met Ala Glu Trp Thr Gly Arg Glu Leu Ser Pro Gly Val Glu Ala<br>                435                      440                      445 | 1704 |
| cag acc gac gag gag ctg cag gac tac atc cgc aag acg cac aac acc<br>Gln Thr Asp Glu Glu Leu Gln Asp Tyr Ile Arg Lys Thr His Asn Thr<br>450                      455                      460 | 1752 |
| gtc tac cac ccc gtg ggc acc gtg cgc atg ggc gcg gtc gag gac gag<br>Val Tyr His Pro Val Gly Thr Val Arg Met Gly Ala Val Glu Asp Glu<br>465                        470                  475                480 | 1800 |
| atg tcc ccg ctc gac ccc gag ctg cgg gtc aag ggc gtc acc ggt ctg<br>Met Ser Pro Leu Asp Pro Glu Leu Arg Val Lys Gly Val Thr Gly Leu<br>                   485                      490                      495 | 1848 |
| cgc gtc ggc gac gcc tcg gtc atg ccc gag cac gtg acc gtc aac ccc<br>Arg Val Gly Asp Ala Ser Val Met Pro Glu His Val Thr Val Asn Pro<br>        500                      505                      510 | 1896 |
| aac atc acc gtc atg atg atc ggc gag cgc tgc gcg gac ctt atc cgc<br>Asn Ile Thr Val Met Met Ile Gly Glu Arg Cys Ala Asp Leu Ile Arg<br>515                        520                      525 | 1944 |

-continued

```
tcc gcc cgc gcc ggt gaa aca acg acg gcg gac gcc gag ctg agc gcg      1992
Ser Ala Arg Ala Gly Glu Thr Thr Ala Asp Ala Glu Leu Ser Ala
    530                 535                 540 gcc ctc gcc taagcgggag cggccagccg cggggcctgt ccggaaccac               2041
Ala Leu Ala
545 ctggcgggcc ccgcatgggg ccggacacaa tgccggtaac taagggtgcg gaagcagtcc     2101 tgcttccaca cccgcgtttt gcacgcccgg ccggcaact  ggcccggccg gctaagccga     2161 aggtcttccg gggcgggcc  ggatcgctgc gggcagtccg tcggccagcc gctgcagcgt     2221 gccggcggta atggcggtgt aggcagggat cgcgtcgggg tagatgtact cgttgcgggc     2281 gtgcgcgccg tcgcccaccg cgcccaggcc gcacaggacc gggatgccga gggcggagac     2341 gaagttggcg tcgctgcccc cgcccaccga ggcggtttcc agctcccggc cctgctcca     2400
```

<210> SEQ ID NO 2
<211> LENGTH: 547
<212> TYPE: PRT
<213> ORGANISM: Arthrobacter globiformis

<400> SEQUENCE: 2

```
Met His Ile Asp Asn Ile Glu Asn Leu Ser Asp Arg Glu Phe Asp Tyr
  1               5                  10                  15

Ile Val Val Gly Gly Ser Ala Gly Ala Val Ala Ala Arg Leu
                 20                  25                  30

Ser Glu Asp Pro Ala Val Ser Val Ala Leu Val Glu Ala Gly Pro Asp
             35                  40                  45

Asp Arg Gly Val Pro Glu Val Leu Gln Leu Asp Arg Trp Met Glu Leu
         50                  55                  60

Leu Glu Ser Gly Tyr Asp Trp Asp Tyr Pro Ile Glu Pro Gln Glu Asn
 65                  70                  75                  80

Gly Asn Ser Phe Met Arg His Ala Arg Ala Lys Val Met Gly Gly Cys
                 85                  90                  95

Ser Ser His Asn Ser Cys Ile Ala Phe Trp Ala Pro Arg Glu Asp Leu
            100                 105                 110

Asp Glu Trp Glu Ala Lys Tyr Gly Ala Thr Gly Trp Asn Ala Glu Ala
        115                 120                 125

Ala Trp Pro Leu Tyr Lys Arg Leu Glu Thr Asn Glu Asp Ala Gly Pro
    130                 135                 140

Asp Ala Pro His His Gly Asp Ser Gly Pro Val His Leu Met Asn Val
145                 150                 155                 160

Pro Pro Lys Asp Pro Thr Gly Val Ala Leu Leu Asp Ala Cys Glu Gln
                165                 170                 175

Ala Gly Ile Pro Arg Ala Lys Phe Asn Thr Gly Thr Thr Val Val Asn
            180                 185                 190

Gly Ala Asn Phe Phe Gln Ile Asn Arg Arg Ala Asp Gly Thr Arg Ser
        195                 200                 205

Ser Ser Ser Val Ser Tyr Ile His Pro Ile Val Glu Gln Glu Asn Phe
    210                 215                 220

Thr Leu Leu Thr Gly Leu Arg Ala Arg Gln Leu Val Phe Asp Ala Asp
225                 230                 235                 240

Arg Arg Cys Thr Gly Val Asp Ile Val Asp Ser Ala Phe Gly Arg Thr
                245                 250                 255

His Arg Leu Thr Ala Arg Asn Glu Val Val Leu Ser Thr Gly Ala Ile
            260                 265                 270
```

```
Asp Thr Pro Lys Leu Leu Met Leu Ser Gly Ile Gly Pro Ala Ala His
            275                 280                 285

Leu Ala Glu His Gly Ile Glu Val Leu Gly Leu Pro Arg Arg Gly
            290                 295                 300

Arg Ala Pro Ala Gly Pro Gly Arg Arg Gly Ala Val Arg Gly Gln
305                 310                 315                 320

Ala Ala His Gly Arg Arg Val His Ala Val Gly Asp Arg His Leu
                325                 330                 335

His Pro His Arg Gly Arg Pro Gly Pro Pro Arg Pro Asp Asp Ala Leu
                340                 345                 350

Arg Leu Arg Ala Val Arg His Glu His Pro Ala Ala Arg Leu Pro His
            355                 360                 365

His Gly Glu Arg Ala Ser Ala Ser Pro Arg Thr Ser Arg Thr Pro Ala
            370                 375                 380

Pro Ala Ala Leu Ser Gly Cys Ala Ala Thr Ser Ala Ile Ser Pro
385                 390                 395                 400

Trp Ser Thr Arg Ala Thr Ser Pro Thr Gln Lys Gly His Asp Met Arg
                405                 410                 415

Val Met Val Ala Gly Ile Arg Lys Ala Arg Glu Ile Ala Ala Gln Pro
                420                 425                 430

Ala Met Ala Glu Trp Thr Gly Arg Glu Leu Ser Pro Gly Val Glu Ala
            435                 440                 445

Gln Thr Asp Glu Glu Leu Gln Asp Tyr Ile Arg Lys Thr His Asn Thr
            450                 455                 460

Val Tyr His Pro Val Gly Thr Val Arg Met Gly Ala Val Glu Asp Glu
465                 470                 475                 480

Met Ser Pro Leu Asp Pro Glu Leu Arg Val Lys Gly Val Thr Gly Leu
                485                 490                 495

Arg Val Gly Asp Ala Ser Val Met Pro Glu His Val Thr Val Asn Pro
                500                 505                 510

Asn Ile Thr Val Met Met Ile Gly Glu Arg Cys Ala Asp Leu Ile Arg
            515                 520                 525

Ser Ala Arg Ala Gly Glu Thr Thr Thr Ala Asp Ala Glu Leu Ser Ala
            530                 535                 540

Ala Leu Ala
545

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 3
ctgtctagat gtaattaaca atggct                                        26

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 4
ccacatatgc atgcattgca ctct                                          24
```

-continued

```
<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 5
aaccatatgc acatcgacaa catc                                              24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 6
gctccatcca gcggtccagc                                                   20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 7
gaaacagtcc tgcttccaca c                                                 21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 8
gcgagctctg cctacaccgc cat                                               23
```

METHOD FOR CREATING OSMOTIC-PRESSURE-TOLERANT PLANT

FIELD OF THE INVENTION

This invention relates to a method for producing plants with novel properties, more specifically, a method for producing salt-tolerant and/or osmotolerant plants which are highly resistant to environmental stresses.

DESCRIPTION OF THE PRIOR ART

One effective way to prevent global warming is greening of uncultivated soils such as desert or salt-accumulated soil. As a means therefor, the development of plants which are resistant to environmental stresses in combination with an engineering solution such as irrigation plays an important role in controlling encroachment of desert, promoting greening and preventing global warming.

Salt accumulation causes the following damages: (1) accumulated salt lowers the water potential in soil to prevent plants from absorbing water; (2) the salt absorbed (penetrated) into plants disturbs their metabolism; (3) salt inhibits the absorption of other ions necessary for viability (Sato, F., Plant Cell Engineering, Supplement, "Environmental Problems and Phytobiotechnology", pp. 33–39, 1994). Especially, the inhibition of water absorption causes plants to lose turgor pressure and close stoma. Thus, photosynthesis is deteriorated and growth is seriously inhibited.

Plants have evolved various mechanisms to adapt themselves to such environments. In a simple adaptation model, plant cells keep an osmotic difference between the inside and outside of the cells in some way, and restore turgor by water absorption. For example, halobacteria, which are not plants however, keep an osmotic balance between the inside and outside by accumulating salt in the cells. In this case, however, it is difficult to adapt them to environmental (osmotic) changes, because intracellular metabolic enzymes per se need to be salt-tolerant.

Therefore, a better adaptation mechanism is the synthesis of a specific compound called "compatible solute" for keeping an intracellular osmosis depending on extrinsic osmotic changes as many salt-tolerant plants do so.

As the compatible solute, bipolar compounds such as glycinebetaine or proline and polyols such as pinitol, sorbitol or mannitol are known. These compounds are characterized by low molecular weight, high water-solubility, low metabolizability, non-influence on metabolism, etc., and are suitable for osmoregulation.

Among others, glycinebetaine (hereinafter referred to as betaine) is noted as a compatible solute found in plants and bacteria which are adaptable to salt-accumulated and/or water-deficient environment. Betaine is thought as a compatible solute found in higher plants such as Chenopodeaceae, Gramineae, Solanaceae, as well as cyanobacteria, Escherichia coli, etc. (for example, see Rhodes, D. and Hanson, A. D., Annu. Rev. Plant Physiol. Plant Mol. Biol. 44:357–3584, 1993). Betaine is an osmoprotective substance which keeps an osmotic balance with environments (Robinson, S. P. and Jones, G. P., Aust. J. Plant Physiol. 13:659–668, 1986) and prevents the dissociation of soluble enzymes due to high salt concentration (Gabbay-Azaria et al., Arch. Biochem. Biophys. 264:333–339, 1988). In addition, betaine can protect photosystem II complex against high salt concentration by stabilization of neighboring proteins and manganese cluster within photosynthetic oxygen-evolving complex (for example, see Murata et al., FEBS Lett. 296:187–189, 1992).

In Escherichia coli and spinach (Spinacia oleracea), betaine is biosynthesized from choline via two steps of oxidation as shown in FIG. 1. E. coli contains two dehydrogenases; one is a membrane-bound oxygen-dependent choline dehydrogenase which oxidizes choline to betainealdehyde (Landfald, B. and Strom, A., J. Bacteriol. 165:849–855, 1986), and the other is a soluble NAD-dependent betainealdehyde dehydrogenase which oxidizes betainealdehyde to betaine (Falkenberg, P. and Strom, A. R., Biochim. Biophys. Acta. 1034:253–259, 1990). In higher plants, it has been demonstrated that betaine is synthesized in the chloroplasts via a similar pathway to E. coli. In spinach (Spinacia oleracea), the first step of oxidation is catalysed by a ferredoxin-dependent choline monooxygenase (Brouquisse, R. et al., Plant Physiol. 90:322–329, 1989) and an NAD-dependent betainealdehyde dehydrogenase which catalyzes the second step of oxidation (Weretilnyk, E. A. et al., Planta. 178:342–352, 1989) has already been isolated. These plants were found to increase the activities of the both enzymes and thereby the amount of betaine under salt stress (for example, see Hanson, A. D. et al., Proc. Natl. Acad. Sci. U.S.A. 82:3678–3682, 1985).

Alternatively, choline oxidase from the gram-positive soil bacterium Arthrobacter globiformis is able to oxidize choline to betaine in one-step oxidation reaction (Ikuta, S. et al., J. Biochem. 82:1741–1749, 1977).

Attempts have been made to confer salt tolerance by integrating such two genes as found in E. coli and higher plants or choline oxidase gene into a plant to allow it constantly express these genes (for example, see Nomura M. et al., Plant Physiol. 107:703–708, 1995). However, no success has been achieved so far in obtaining a salt-tolerant and/or osmotolerant plant by integrating such genes into a plant, especially a higher plant expressing them stably.

Choline oxidase is commercially available, but its amino acid sequence has not been determined. Therefore, it would be highly desirable to determine a genetic sequence encoding choline oxidase which can efficiently convert choline into betaine and to integrate it into a plant to allow it to stably express said sequence, whereby producing a plant which is tolerant to environmental (osmotic) changes such as high salt concentration.

SUMMARY OF THE INVENTION

After profound study to solve the above problems, the present inventors succeeded in isolating a novel gene encoding choline oxidase (The Japanese Society of Plant Physiologist, Annual meeting of 1994, the 34th Symposium held Mar. 28–30, 1994) and integrating it into cyanobacteria, brassicaceous and gramineous plants to obtain salt-tolerant and/or osmotolerant plants.

Accordingly, this invention provides a method for producing salt-tolerant and/or osmotolerant plants, which comprises the step of transforming a plant with a recombinant vector carrying a gene encoding choline oxidase, as well as the salt-tolerant and/or osmotolerant plants obtained by said method.

BRIEF DESCRIPTION OF THE DRAWINGS

FIG. 11 shows Western blot analysis (photograph of electrophoresis) of choline oxidase in soluble fractions of the wild-type and transformant plants of Arabidopsis. Lane 1: choline oxidase from a commercial product of *Arthrobacter globiformis* (Sigma Chemical Co., St. Louis, Mo., USA); lane 2: soluble fractions of the wild-type plant; lane 3: soluble fractions of a transformant plant.

FIG. 13 shows the effect of sorbitol on the growth of Arabidopsis. The wild-type (W) and transformant (T) plants in the presence of 100, 200 and 400 mM sorbitol are shown (photographs showing the morphology of the organisms).

DETAILED DESCRIPTION OF THE INVENTION

Figure 1:
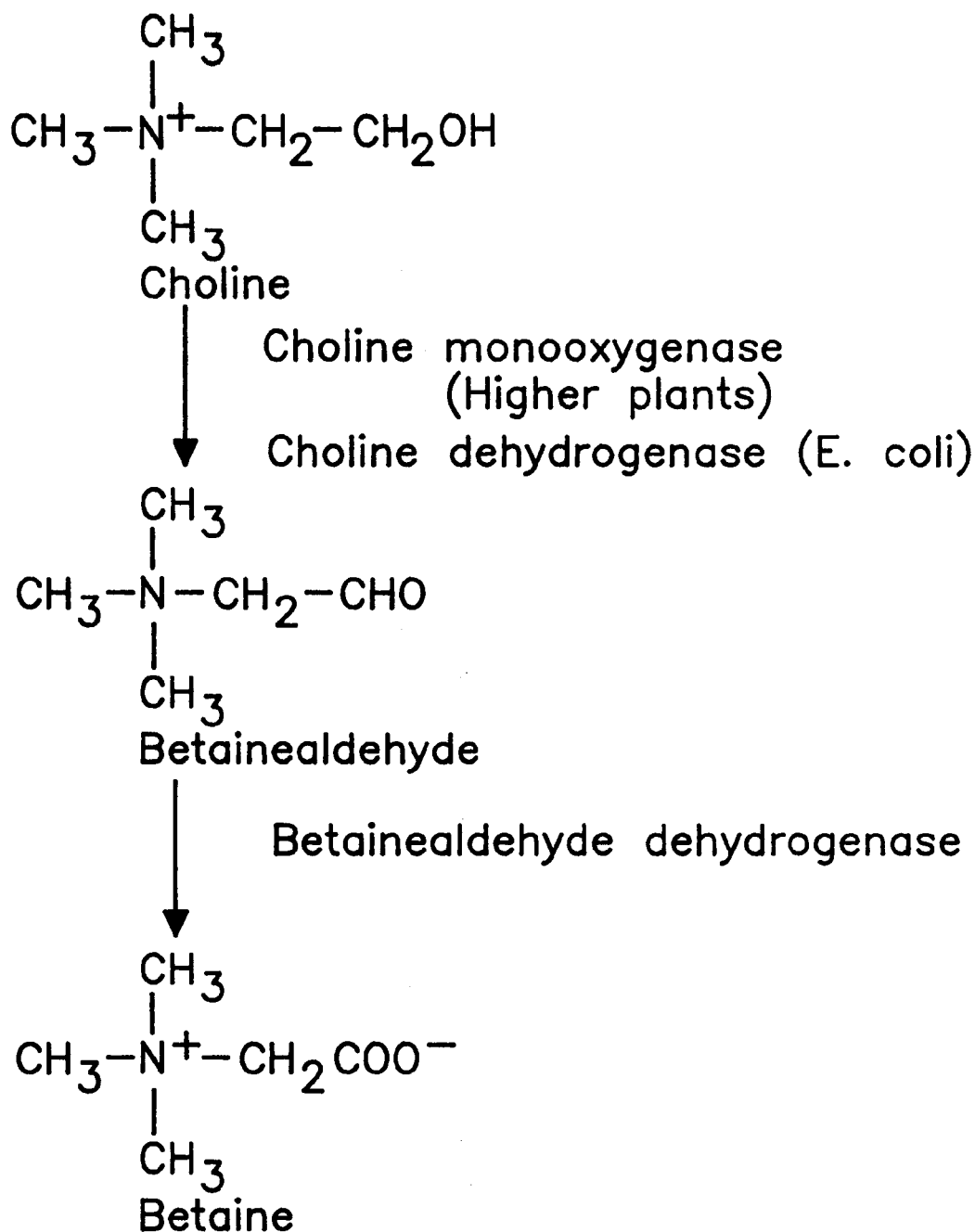
FIG. 1 is a schematic representation showing the oxidation process from choline to betaine.

The gene encoding choline oxidase used in this invention is a gene which encodes a protein capable of converting choline into betaine in a one-step reaction and which may be derived from gram-positive soil bacteria of the genus Arthrobacter. For example, it may be preferably derived from *Arthrobacter globiformis* and *Arthrobacter pascens*, especially *Arthrobacter globiformis*.

The present inventors successfully cloned the codA gene encoding choline oxidase from *Arthrobacter globiformis* and determined its nucleotide sequence (SEQ ID NO:1). The codA gene contains an open reading frame of 1641 bp, which encodes 547 amino acids. The nucleotide sequence and amino acid sequence of the codA gene are shown as SEQ ID NO. 1 and SEQ ID NO:2.

Plants can be transformed with such a choline oxidase-coding gene integrated into appropriate vectors. Then, the gene can be expressed in the plants by introducing into these vectors an appropriate promoter or a sequence responsible for the expression of character.

Any gene having a nucleotide sequence resulting from addition, deletion or substitution of the nucleotide sequence encoding the amino acid of SEQ ID NO. 1 and SEQ ID NO:2 or a part thereof may be used as the gene according to this invention so far as it encodes a polypeptide showing choline oxidase activity.

According to the method of this invention, salt tolerance and/or osmotolerance can be conferred to a large variety of plants ranging from cyanobacteria to higher plants. Cyanobacteria are widely used as model organisms of higher plants because they have basically the same photosynthetic mechanism as higher plants and they are easily transformed to give the results in a short time. Some transformant-type cyanobacteria readily incorporate foreign DNA into their cells to cause efficient recombination. Such cyanobacteria include Synechococcus PCC7942, Synechococcus PCC6301 (ATCC 27144) and Synechocystis PCC6803 (ATCC 27184) (Protein, Nucleic Acid, Enzyme, Vol.35, No.14, pp.2542–2551, 1991; Crit. Rev. Microbiol. Vol.13, No.1, pp.111–132, 1985).

Higher plants include dicotyledons and monocotyledons. In Examples described below, highly salt-tolerant and/or osmotolerant plants could be obtained from a brassicaceous plant as a dicotyledon, but it is not limitative and other families and genera of dicotyledons may be used. The method of this invention may also be applicable to monocotyledons. It was found that a monocotyledonous plant rice, which originally lacks betaine-synthesizing ability, gained this ability, and therefore salt tolerance after transformation according to the method of this invention.

The vectors into which the choline oxidase-coding gene is integrated and the procedures for transformation and selection of the transformant plant materials can be appropriately chosen dependent on the nature of the plant to be transformed.

For example, plasmids such as pUC303 can be used for cyanobacteria. Then, the transformants having desired properties can be selected by the antibiotics resistant genes inserted into these plasmids. This invention succeeded in obtaining the plants which stably show salt tolerance and/or osmotolerance by transforming the cyanobcterium Synechococcus PCC7942 with the codA gene encoding choline oxidase from *Arthrobacter globiformis*.

When the Synechococcus PCC7942 transformed with the codA gene was cultivated on a medium supplemented with choline chloride, the Synechococcus was found to take up exogeneously supplied choline and convert it into betaine. In view of the report that choline transport is induced by salt stress in several salt-tolerant bacteria, resulting in accumulation of higher level of betaine (Kaenjak, A. et al., J. Bacteriol. 175:2400–2406, 1993), the influence of salt stress on betaine accumulation was examined by treating the transformant Synechococcus produced by this invention with NaCl at various concentrations. However, the influence of NaCl concentration on betaine accumulation was not significantly observed, suggesting that the transporter for choline uptake in Synechococcus is not specifically induced by salt stress.

It has also been reported that betaine not only acts as an osmoprotectant but also plays an essential role in protection of photosynthetic mechanism in photoautotrophic organisms (Murata, N. et al., FEBS Lett. 296:187–189, 1992). The Synechococcus transformed according to this invention was cultivated in the presence of high concentration NaCl or sorbitol to examine growth, chlorophyll content and photosynthetic activity. As a result, the transformant Synechoccocus grew well in the presence of either high concentration salt or sorbitol and also showed the similar results for chlorophyll content and photosynthetic activity, as compared with the control non-transformant in which growth, chlorophyll content and photosynthetic activity were all inhibited. These results mean that excellent salt tolerance and osmotolerance were conferred to the Synechococcus transformed with the gene encoding choline oxidase according to the method of this invention.

Dicotyledons may be transformed by gene introduction technique using protoplasts or a part of tissue. In case of the gene introduction using tissue pieces, the Ti plasmid from Agrobacterium may be used. Tissue pieces of a callused plant may be infected with Agrobacterium bearing protoplasts into which the choline oxidase-coding gene has been integrated, selected by resistance to an antibiotic such as kanamicin, and then differentiated in shoots to give a transformant plant.

In this invention, a salt-tolerant and/or osmotolerant plant was obtained by transforming the brassicaceous plant Arabidopsis thaliana with the choline oxidase-coding gene as follows.

A binary vector plasmid pGAH-codA carrying the codA gene was prepared and integrated into *Agrobaterium tumefaciens* EHA101 bearing the Ti plasmid. *Hypocotyl calli* of Arabidopsis were infected with the resultant Agrobacterium EHA101 (pGAH/codA) incorporating the codA gene, then shoots were formed and selected by kanamycin and hygromycin resistance to induce roots and to form seeds. The plants obtained from said heterozygous T2 seeds were self-fertilized to give homozygous T3 individuals, which were sown to form transformant plants. These transformant plants showed that choline oxidase had been transported to the chloroplasts. The transformant plants grew well even in the presence of high concentration sodium chloride or sorbitol.

The monocotyledonous plant rice (*Oryza sativa* L. cv. *Nippon bare*) can be transformed with two chimeric codA genes prepared on the plasmid pUC119, which are localised on cytosol or plastide after translation under transcriptional contol of the cauliflower mosaic virus 35S promoter. Both of the chimeric genes include a rice-derived intron in the 5' non-translated sequence in order to enhance the expression.

The transformant rice can be produced by the following procedure. Namely, the transformant plant can be obtained by introducing said chimeric codA genes into suspension culture cells from scutellum calli of rice seeds together with the selection marker hygromicin-resistant gene by a particle gun device, then selecting the transformed calluses based on the antibiotics resistance, and redifferentiating them into a plant.

Although the wild-type rice lacks betaine-synthesizing ability, the rice transformed by the method of this invention gained betaine-synthesizing ability. The transformant rice expressing the codA gene grew equally to the non-transformed plant without showing any apparent abnormality under the both of geoponic and hydroponic conditions. This may conclude that hydrogen peroxide formed as a by-product of betaine synthesis was efficiently detoxified in the cells.

Moreover, salt tolerance tests of the transformants cultivated on water with NaCl showed that the inhibition of photosynthetic activity in the transformants was slower than observed in the wild type. This is the first case in which rice has gained betaine-synthesizing ability through a genetic engineering procedure.

These results show that various plants transformed with recombinant vectors carrying the gene encoding choline oxidase have an excellent salt tolerance.

According to this invention, salt-tolerant and/or osmotolerant transformant plants which are highly resistant to environmental stresses can be obtained. The range of plants to which can be conferred salt tolerance and/or osmotolerane by the method of this invention is very wide, from cyanobacteria to higher plants. Especially, this invention is the first case in which salt-tolerant and/or osmotolerant transformant plants were obtained from monocotyledons including most of main crops and expected to be applied in a very wide range.

The following examples further explain this invention in detail, but are not intended to limit the scope of this invention.

EXAMPLES

Example 1

Transformation of the Cyanobacterium
Synechococcus PCC7942 with the codA Gene (1) Cloning of the codA Gene The choline oxidase gene was isolated from *Arthrobacter globiformis* by the method described in the Abstracts of Oral Reports in the abstracts, the 34th annual meeting of the Japanese Society of Plant Physiologists, 1994. In brief, 1) choline oxidase is fragmented with cyanogen bromide, 2) the N-terminal amino acid sequences of appropriate fragments are determined, 3) an appropriate part is selected from said amino acid partial sequences to synthesize oligonucleotides corresponding thereto, 4) a partial sequences of the choline oxidase gene is amplified by PCR (Polymerase Chain Reaction) using these oligonucleotides as primers, 5) the amplified partial sequence of the choline oxidase gene is used as a probe to screen the genomic DNA library of *Arthrobacter globiformis*.

Thus obtained positive clones were subcloned into the plasmid pBluescript (SK+) (Stratagene) to isolate positive clones, which were subjected to Southern blot analysis. A 3.6 kbp XbaI-XhoI fragment which hybridized to said probe was subcloned into pBluescript and mapped with restriction enzymes. The nucleotide sequence of the region spanning from the first SalI-site to XhoI-site (about 2.5 kbp) was determined.

The results showed that the choline oxidase gene contains an open reading frame of 1641 bp which encodes a polypeptide of 547 amino acid residues. The amino acid sequence and the nucleotide sequence of the choline oxidase-coding gene are shown as SEQ ID NO. 1 and SEQ ID NO:2.

(2) Transformation of Synechococcus PCC7942 with the codA Gene

The plasmid pBluescript carrying the codA gene was digested with BstEII (position −40 from the initiation of translation) and SmaI (downstream of the stop codon) restriction enzymes. The BstE II-cohesive end was filled in by Klenow fragment (Takara, Tokyo, Japan). The blunt-ended fragment containing the coding region of the codA gene and a putative ribosome binding site was inserted into the SmaI site of the plasmid pAM1044. The correct orientation of the gene, which is supposed to be expressed under control of the conII promoter of pAM1044, was confirmed by restriction analysis. The conII promoter is the consensus sequence of promoters of *E. coli*, which contains the base sequences TTGGACA (−35) and TATAAT (−10).

The plasmid pAM1044 and the plasmid containing the codA gene were used for transformation of Synechococcus PCC7942 by the method of Elhai et al. The resultant transformant was designated as the strain PAMCOD. Synechococcus PCC7942 transformed with pAM1044 alone was used as a control and designated as the strain PAM.

Figure 2A:
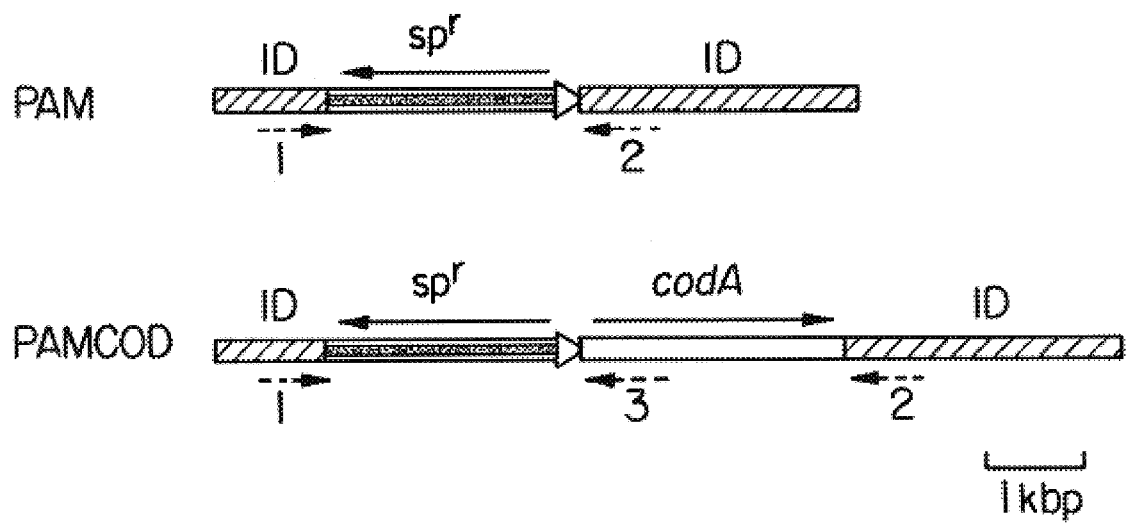
FIG. 2A is a schematic representation showing the constructs used for transformation of Synechococcus PCC7942. PAM refers to Synechococcus PCC7942 transformed with pAM1044, and PAMCOD refers to Synechococcus PCC7942 transformed with pAM1044 carrying the codA gene. Dashed arrows indicate the primers used for PCR. Triangles represent the conII promoter. Arrows indicate the orientation of the genes.

Selection of the transformants was done on the BG11 agar plate containing spectinomycin at 30 μg/ml. After several inoculations of a single colony to fresh BG11 plates containing spectinomycin, the complete insertion of the spectinomycin-resistant gene and the codA gene into all the copies of the chromosomes was confirmed by PCR (Polymerase Chain Reaction) using the primers indicated in FIG. 2A. The complete insertion of the spectinomycin-resistant gene and the codA gene into the chromosomes of Synechococcus was confirmed by PCR using a combination of primers 1 and 2.

Example 2

Confirmation of the Gene Inserted into Transformants

The DNAs from the wild-type strain, the strain PAM and the strain PAMCOD of Synechococcus PCC7942 were used as templates for PCR, and the amplified products were analyzed by SDS-PAGE. The results are shown in FIG. 2B.

Figure 2B:
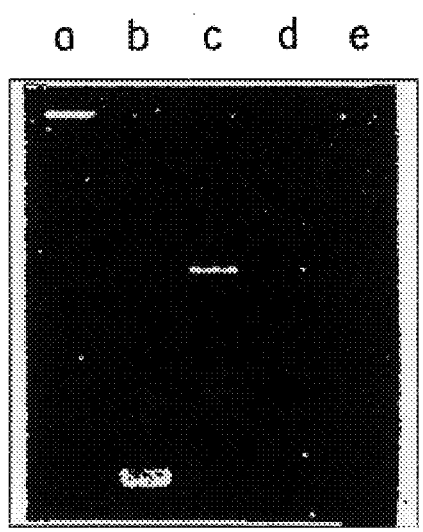
FIG. 2B is an SDS-PAGE representation (photograph of electrophoresis) showing the complete replacement of chromosomes by the spectinomycin-resistant gene and codA gene in DNA of Synechococcus PCC7942. Lane a: λ-HindIII/φx174-HaeIII fragment; lane b: the wild-type strain of Synechococcus PCC7942; lane c: the strain PAM; lanes d and e: the strain PAMCOD (lanes b, c and d show the results of PCR with primers 1 and 2, and lane e shows the results of PCR with primers 1 and 3).

A PCR performed on the DNA from the wild-type strain revealed an amplified product of about 400 bp (FIG. 2B, lane b). When the DNA from the strain PAM was used as a template, a band of about 2.4 kb appeared, representing the insertion of pAM1044 into the chromosomes. The absence of the band of about 400 bp, which was observed in the wild-type strain, confirms the complete replacement of the native chromosomes by the mutated chromosomes in the strain PAM.

When the DNA from PAMCOD was used as a template, the band corresponding to the wild-type chromosomes was not observed (FIG. 2B, lane c). However, the expected band of about 4.1 kb was not amplified, either, likely due to a large size of the insert and a high GC content in the codA sequence. Therefore, primer 3 corresponding to the coding region of the codA gene (FIG. 2A) was used in combination with primer 1. The expected band of about 2.6 kb was amplified (FIG. 2B, lane d), indicating the presence of the codA gene in the chromosomes of the strain PAMCOD.

Example 3

Expression of the codA Gene in the Synechococcus Strain PAMCOD

Figure 3:
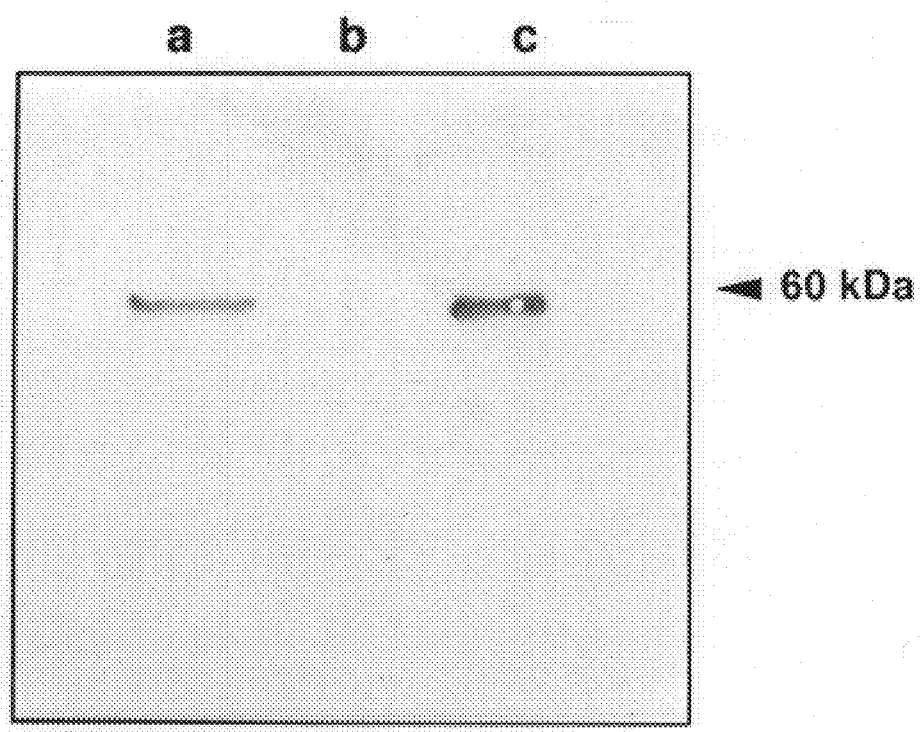
FIG. 3 is a Western blot analysis representation (photograph of electrophoresis) showing the expression of choline oxidase in the Synechococcus strains PAM and PAMCOD. Lane a: protein extracts from the strain PAMCOD; lane b: protein extracts from the strain PAM; lane c: purified choline oxidase.

The expression of the codA gene in the strain PAMCOD obtained in Example 1 was examined by Western blot analysis using polyclonal antiserum raised against the purified choline oxidase. The results are shown in FIG. 3. Signals were detected in the protein extracts obtained from the strain PAMCOD (lane a) and purified choline oxidase (lane c) at the position of 60 kDa. Such a signal was not detected in the protein extracts obtained from the strain PAM (lane b). This result confirms that the codA gene was expressed under control of the conII promoter in Synechococcus PCC7942.

Example 4

Analysis of Betaine Concentration in Cells

The transformed cells were grown in one liter of BG11 medium supplemented with 5 mM choline chloride. Salt stress was given by adding various concentrations of NaCl. The harvested cells were treated with 1M $H_2SO_4$ at 25° C. for 20 hours and betaine was recovered from the mixture by means of the periodate precipitation technique (Wall, J.S. et al., Analyt. Chem. 32:870–874, 1960). The betaine periodate was dissolved in 1ml of methanol-$d_4$ (Wako Pure Chemical Industries, Osaka, Japan) containing 2 mM 2-methyl-2-propanol (Wako Pure Chemical Industries) as an internal standard. This solution was transferred to an NMR tube and $^1$H NMR spectra were measured with a Bruker AMX 360 Wb. Betaine was quantified by comparing the integrated peaks with a standard curve.

The concentration of betaine in the cells of the strain PAMCOD was determined on the basis of the cell volume estimated from the electron micrograph of negatively stained cells. The cytoplasm of a single cell had a cylindrical shape of 2.14 μm in length and 0.82 μm in diameter and the cell volume was estimated to be approximately 1.13 μm$^3$.

The following Table 1 shows the changes in betaine concentration in the cells with the increase of NaCl concentration in the medium. Any trace of betaine could not be detected in the strain PAM lacking the codA gene. The betaine concentration in the cells of the strain PAMCOD ranged from 60 to 90 mM. Betaine accumulation in the cells of the strain PAMCOD was not significantly affected by NaCl concentration.

TABLE 1

| NaCl (M) | PAM (mM) | PAMCOD (mM) |
|---|---|---|
| 0 | 0 | 67 ± 3 |
| 0.2 | 0 | 73 ± 4 |
| 0.3 | 0 | 86 ± 2 |

Example 5

Tolerance of the Synechococcus Strain PAMCOD to salt and Osmotic Stresses

The tolerance toward salt and osmotic stresses of the cells were evaluated by measuring cell growth, chlorophyll content and photosynthetic activity. Cells of the Synechococcus strains PAM and PAMCOD were precultivated in the BG11 medium supplemented with 1 mM choline chloride at 30° C. for 3 days and the cultures were transferred to the BG11 medium supplemented with 1 mM choline chloride containing 0.4M NaCl or 0.8M sorbitol. Cell growth was monitored by optical density at 730 nm. Chlorophyll content was determined by the method described by Arnon et al. (Biochim. Biophys. Acta. 357:231–245, 1974). The photosynthetic oxygen evolution was measured by monitoring oxygen concentration with a Clark-type oxygen electrode using 1 mM 1,4-benzoquinone and 1 mM $K_3Fe(CN)_6$ as electron acceptors. The same cells were cultivated on the medium free from NaCl as a control.

Figure 4:
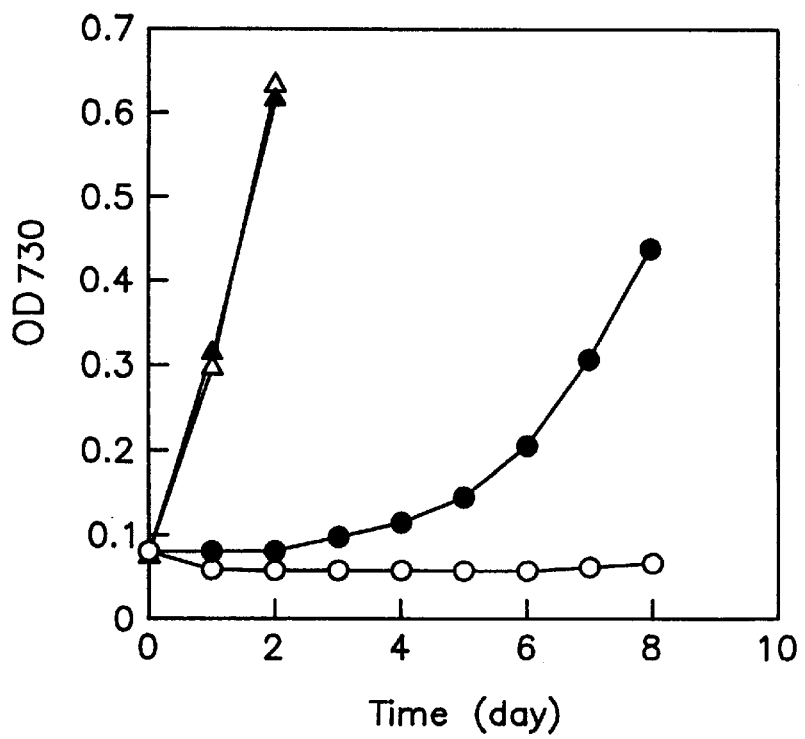
FIG. 4 shows the effect of NaCl on growth. Growth of the Synechococcus strains PAM (○) and PAMCOD (●) in the presence of 0.4M NaCl is shown. For comparison, growth of the Synechococcus strains PAM (Δ) and PAMCOD (▲) cultivated on the medium free from NaCl is also shown.
Figure 5:
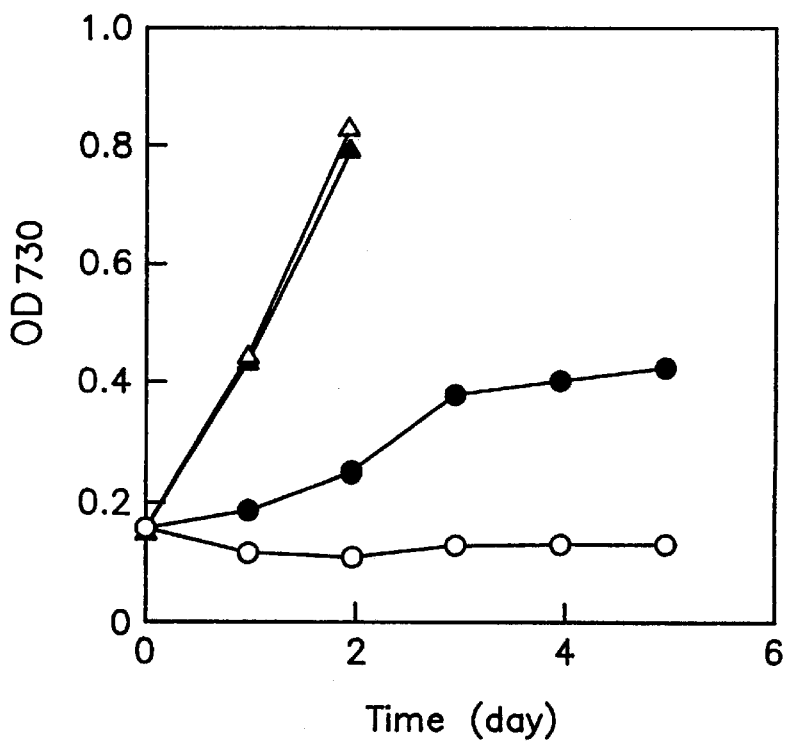
FIG. 5 shows the effect of sorbitol on growth. Growth of the Synechococcus strains PAM (○) and PAMCOD (●) in the presence of 0.8M sorbitol is shown. For comparison, growth of the Synechococcus strains PAM (Δ) and PAMCOD (▲) cultivated on the medium free from sorbitol is also shown.

The results of the cell growth test in the presence of NaCl are shown in FIG. 4 and the results of the cell growth test in the presence of sorbitol are shown in FIG. 5. The growth of the strain PAM was inhibited by high salt and osmotic stresses, while the strain PAMCOD could grow under these conditions.

Figure 6:
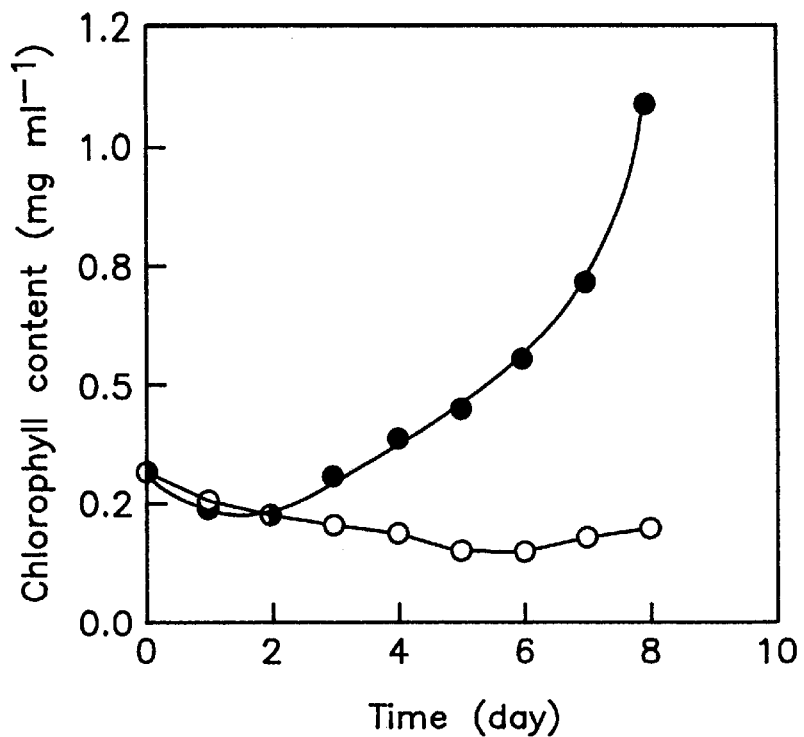
FIG. 6 shows the effect of NaCl on chlorophyll content. Chlorophyll contents of the Synechococcus strains PAM (○) and PAMCOD (●) in the presence of 0.4M NaCl are shown.
Figure 7:
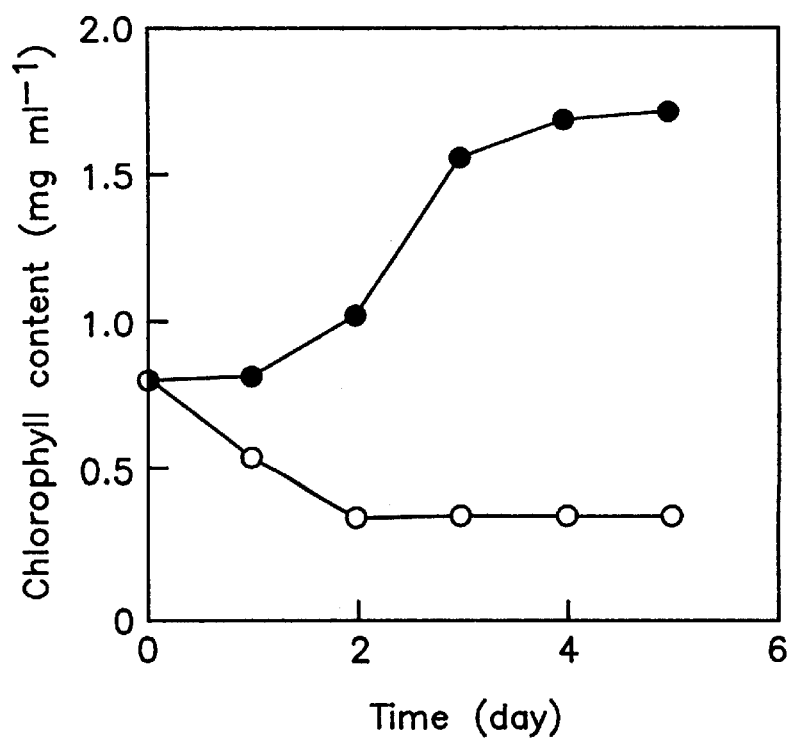
FIG. 7 shows the effect of sorbitol on chlorophyll content. Chlorophyll contents of the Synechococcus strains PAM (○) and PAMCOD (●) in the presence of 0.8M sorbitol are shown.

The results of the chlorophyll content test in the presence of NaCl are shown in FIG. 6 and the results of the chlorophyll content test in the presence of sorbitol are shown in FIG. 7. The results of this test were similar to those of the cell growth test. The chlorophyll content in the strain PAM treated with a high concentration salt gradually decreased and the chlorophyll content in the strain PAM treated with 0.8M sorbitol rapidly decreased, but on the contrary, the strain PAMCOD contitued to grow even under salt or sorbitol treatment.

Figure 8:
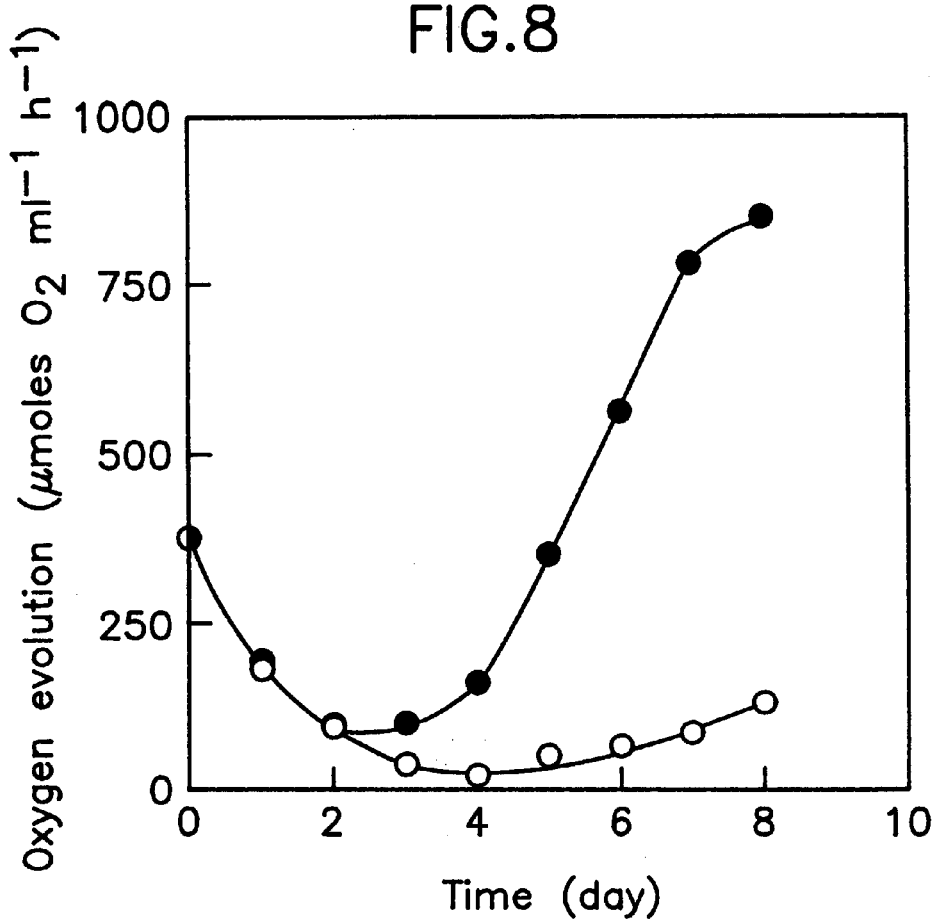
FIG. 8 shows the effect of NaCl on photosynthetic activity. Oxygen evolution levels from the Synechococcus strains PAM (○) and PAMCOD (●) in the presence of 0.4M NaCl are shown.

The results of the photosynthetic activity test in the presence of NaCl are shown in FIG. 8. Photosynthetic activity of the strain PAM was strongly inhibited by salt stress. In contrast, photosynthetic activity of the cells of the strain PAMCOD was temporarily inhibited at the early stage of salt treatment, but afterward recovered and continuously increased. The similar results were obtained in the photosynthetic activity test in the presence of sorbitol. Interestingly, the temporary decrease of photosynthetic activity was not observed when the cells of the strain PAMCOD were treated with 0.8M sorbitol.

Example 6

Preparation of a Binary Vector Plasmid Carrying the codA Gene

The rbcS (ribulose 1,5-bisphosphate carboxylase small subunit) transit signal XbaI-NdeI fragment (about 200 bp) from tobacco (Nicotiana sylvestris) was amplified by PCR using 5' CTGTCTAGATGTAATTAACAATGGCT3' (SEQ ID NO:3) and 5' CCACATATGCATGCATTGCACTCT3' (SEQ ID NO:4) as primers to introduce the XbaI and NdeI sites.

Then, the N-terminal-BamHI fragment (about 100 bp) of the codA gene was amplified by PCR using 5' AACCATATGCACATCGACAACATC3' (SEQ ID NO:5) and 5' GCTCCATCCAGCGGTCCAGC3' (SEQ ID NO:6) as primers to introduce the NdeI site. The BamHI-SmaI fragment (about 1.6 kbp) of the codA gene was prepared by restriction enzymes. Further, the SmaI-C-terminal fragment (about 80 bp) of the codA gene was amplified by PCR using 5' GAAACAGTCCTGCTTCCACAC3' (SEQ ID NO:7) and 5' GCGAGCTCTGCCTACACCGCCAT3' (SEQ ID NO:8) as primers to introduce the SacI site.

The GUS (β-glucuronidase) gene in the binary vector plasmid pBI221 was replaced by these fragments.

Figure 9:
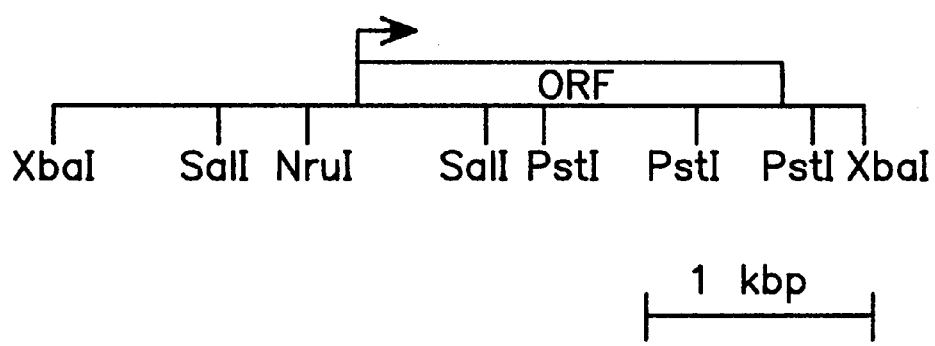
FIG. 9 is a schematic representation showing the restriction enzyme map of the codA gene.

The restriction enzyme map of the codA gene is shown in FIG. 9.

Figure 10:
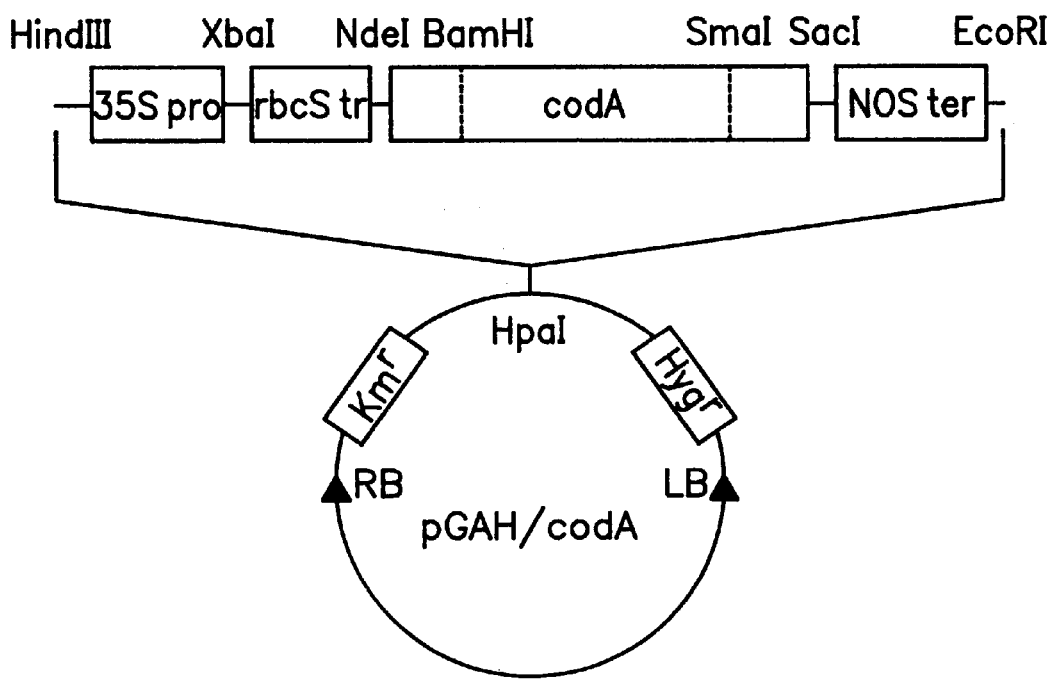
FIG. 10 is a schematic representation showing the structure of the binary vector plasmid pGAH/codA used for transformation of Arabidopsis.

The HindIII-EcoRI fragment containing the 35S promoter and the NOS (nopalin synthase) terminator of cauliflower mosaic virus was introduced into the binary vector plasmid pGAH to prepare the plasmid pGAH/codA (FIG. 10). This plasmid contains kanamycin- and hygromycin-resistant genes.

Example 7

Introduction of the Binary Vector Plasmid into Agrobacterium

The *Agrobacterium tumefaciens* EHA 101 bearing the Ti plasmid was mixed with the binary vector plasmid pGAH/codA obtained in Example 6, then freezed and thawed, and screened on the LB plate containing tetracycline and kanamycin. The resultant Agrobacterium in which the codA gene has been integrated was designated as EHA101 (pGAH/codA).

Example 8

Transformation of Arabidopsis

The *Arabidopsis thaliana* strain WS was germinated to prepare a hypocotyl segment. This hypocotyl was callused on B5 medium (ICN Biochemicals) (pH 5.7) containing 0.05 mg/l of kinetin (Wako Pure Chemical Industries) and 0.5 mg/l of 2,4-D (Wako Pure Chemical Industries) to form *hypocotyl calli*.

Then, the calli were infected with the codA-containing Agrobacterium EHA101 (pGAH/codA) prepared in Example 7 and cocultivated. After detoxification of Agrobacterium by B5 medium containing 250 mg/l of vancomycin, 500 mg/l of carbenicillin and 200 mg/l of Claforan, the cultures were transferred to a differentiation medium (B5 medium containing 25 mg/l of kanamycin and 15 mg/l of hygromycin) to form shoots. Then, kanamycin- and hygromycin-resistant shoots were selected to induce roots and to form seeds. The resultant T2 seeds are heterozygous transformed in only one of the chromosomes.

Then, the plants obtained from the T2 seeds were self-fertilized and selected by kanamycin and hygromycin to give homozygous T3 seeds.

The plants of the wild-type and transformant strains were grown in a medium (pH 5.2) containing 0.1% HYPONEX (Hyponex Corporation, Marysville, Ohio, USA) at 22° C. for 30 days on water or soil consisting of vermiculite and perlite with illumination of 75 $\mu mol.m^{-2}.S^{-1}$ for 16 hours in a day and in a dark room for the remaining 8 hours unless otherwise indicated, and then used for experiments.

Example 9

Immunological Study of the Expressed Choline Oxidase

An antibody was raised against choline oxidase according to the method described by the present inventors in literature (Deshniumn, P. et al., Plant Mol. Biol. 29:897–907, 1995).

Leaf from each 20-day old plant of the wild-type and transformant strains of Arabidopsis thaliana was ground in a microcentrifuge at 0° C. and the homogenates were centrifuged at 10,000× g for 10 minutes to prepare soluble fractions. The soluble protein of the supernatant was separated by SDS-PAGE and transferred to a nylon membrane (Immobilon PVDF; Millipore, Bedford, Mass., USA). The membrane was incubated with the antibody against choline oxidase and detected with a system consisting of biotinylated secondary antibody, avidin and biotinylated horse radish peroxidase (ABC Kit; Vectastain, Burlingane, Calif., USA).

The results of Western blot analysis are shown in FIG. 11. The presence of an immune responsive protein of 64 kDa corresponding to choline oxidase was identified. A small amount of protein of 70 kDa corresponding to the precursor of choline oxidase and the rbcS transit peptide were also observed. These results show that the codA gene was correctly integrated and expressed in the chromosomes and that the expressed precursor was processed into a manure protein.

Then, localization of the expressed choline oxidase in the plant was detected with the antibody against choline oxidase by a method described in literature (Mustardy, L. et al., Plant Physiol. 94:334–340, 1990). A small piece of young leaf from the plant was fixed with 1% glutaraldehyde in 0.1M sodium phosphate buffer (pH 7.2) for one hour. After rinsed with the same buffer, the sample was dehydrated with ethanol and placed in Lowicryl K4M resin (TAAB Laboratories Equipment Ltd., Berkshire, U.K.). Immuno-gold labeling was conducted by a method described in literature (Mustardy et al., supra).

As a result, the expressed choline oxidase was found to be localized in stroma of the chloroplasts, indicating that choline oxidase had been transported to the chloroplasts.

Example 10

Determination of Betaine and Chlorophyll Contents in Transformant Plants

Betaine content in leaf of the plants was calculated by measuring NMR spectra of the quaternary ammonium compound (Wall, J. et al., Analyt. Chem. 32:870–874, 1960). 5 g of leaf of the wild-type strain and transformant plants were powdered in liquid nitrogen by a ceramic motor. This powder was suspended in 25 ml of 1.0M $H_2SO_4$ and incubated at 25° C. for 2 hours. After unsoluble matters were removed, the supernatant was recovered by centrifugation at 1000× g for 10 minutes. The supernatant was combined with 10 ml of $KI-I_2$ solution and incubated at 0° C. for 2 hours. Peridodide-adducts of betaine and choline were recovered by centrifugation at 1000× g for 30 minutes and dissolved into 0.5 ml of $CD_4OH$ (Wako Pure Chemical Industries) containing 0.5 mM 2-methyl-2-propanol (Wako Pure Chemical Industries) as an internal standard to measure $^1H$ NMR spectra. Two main peaks corresponding to betaine and choline were observed, and the integrated betaine peaks were used for determination of the concentration.

Chlorophyll content in leaf was measured by the following procedure. Leaf (1 g) was powdered in liquid nitrogen by a ceramic motor. The powder was suspended in 10 ml of acetone:water (4:1, v/v). After incubation for 30 minutes, unsoluble matters were removed and the supernatant was subjected to spectrophotometry (Arnon, D. I. Plant Physiol. 24:1–15, 1949).

As a result, the both of betaine and choline were observed in the transformant plant, while only choline was observed in the wild-type strain. Betaine content was 1.0 μmol/g fresh leaf. Chlorophyll content was 0.3 μmol/g fresh leaf.

Example 11

Figures 12A, 12B:
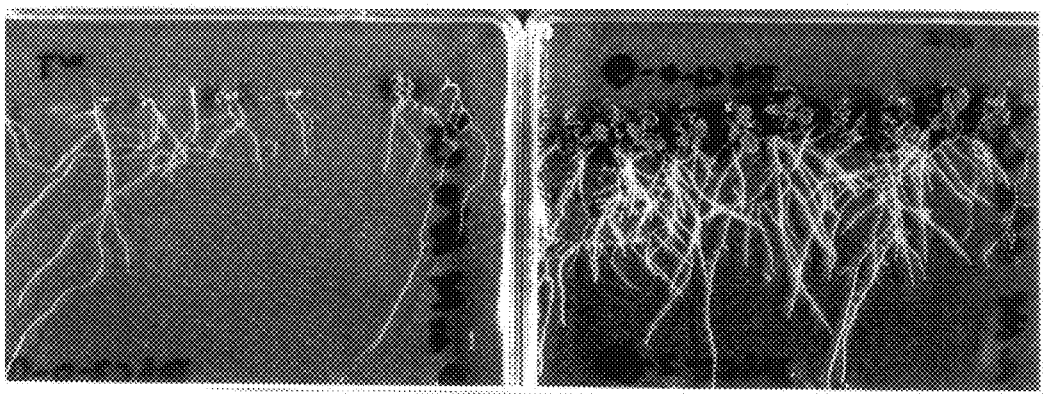
FIGS. 12A–12B show the effect of NaCl on the growth of Arabidopsis. The wild-type (A) and transformant C1-0 (B) plants in the presence of 60 mM NaCl are shown (photographs showing the morphology of the organisms).

Tolerance of Transformant Arabidopsis to Salt and Osmotic Stresses (1) Tolerance to Salt Stress The T3 seeds obtained in Example 8 were inoculated on Murashige & Skoog's medium gelled with 0.5% gellan gum to compare germination, rooting and growth of cotyledons. On the medium free from NaCl, any difference was not found between the wild-type strain and the transformant plants. On the medium containing 60 mM sodium chloride, however, one of the transformant plants C1-0 grew relatively well to show salt tolerance as compared with the wild-type strain which poorly grew (FIG. 12).

On the medium containing 100mM sodium chloride, the wild-type strain stopped growing and its leaves whitened 10 days after germination. However, the transformant plants continued to grow while keeping green. Especially, roots of the transformant plants grew remarkably better than those of the wild-type strain. The wild-type strain and the transformant strain plants equally grew in a control test free from 100mM sodium chloride, confirming that the transformant plants gained the ability to grow under salt stress conditions.

(2) Tolerance to Osmotic Stress

The seeds of the wild-type strain and the transformant plants were sterized and inoculated on semi-solid media containing 100, 200 and 400 mM sorbitol. The cultures were placed in an incubator maintained at 22° C. with illumination of 75 μmol/m²/second for 16 hours in a day and in a dark room for the remaining 8 hours, and regularly observed. The state on the day 15 is shown in FIG. 13 (W on the left represents the wild-type strain and T on the right represents the transformant plants). At a sorbitol concentration of 100 mM, some wild-type strains showed no germination or its leaves whitened even if they germinated. However, the transformant plants continued to grow while keeping green. At a concentration of 200 mM, growth of the both strains was inhibited, but the inhibition degree of the transformant plants was lower than that of the wild-type strain, and especially, the growth of roots of the transformant plants was remarkably better than that of the wild-type strain. At a concentration of 400 mM, the wild-type strain showed no germination and the transformant plants showed no germination, either, or scarcely grew even if they germinated.

Example 12

Photosynthetic Activity of Transformant Plants Under Salt Stress

The influence of salt stress on photosynthetic system II activity of mature leaves was measured by monitoring fluorescence of chlorophyll.

The wild-type strain and the transformant strain plants grown on a control medium were transferred to HYPONEX medium containing 400 mM sodium chloride and incubated under the light or dark conditions described above. After a determined time, leaves were taken from the plants and the efficiency of photosynthetic system II was measured as a ratio of variable chlorophyll fluorescence to maximum chlorophyll fluorescence (Fv/Fm) by using a pulse intensity-modulated fluorometer (PAM-2000; Walts, Effeltrich, Germany) (Annu. Rev. Plant Physiol. Plant Mol. Biol. 42:313–349, 1991).

Figure 14:
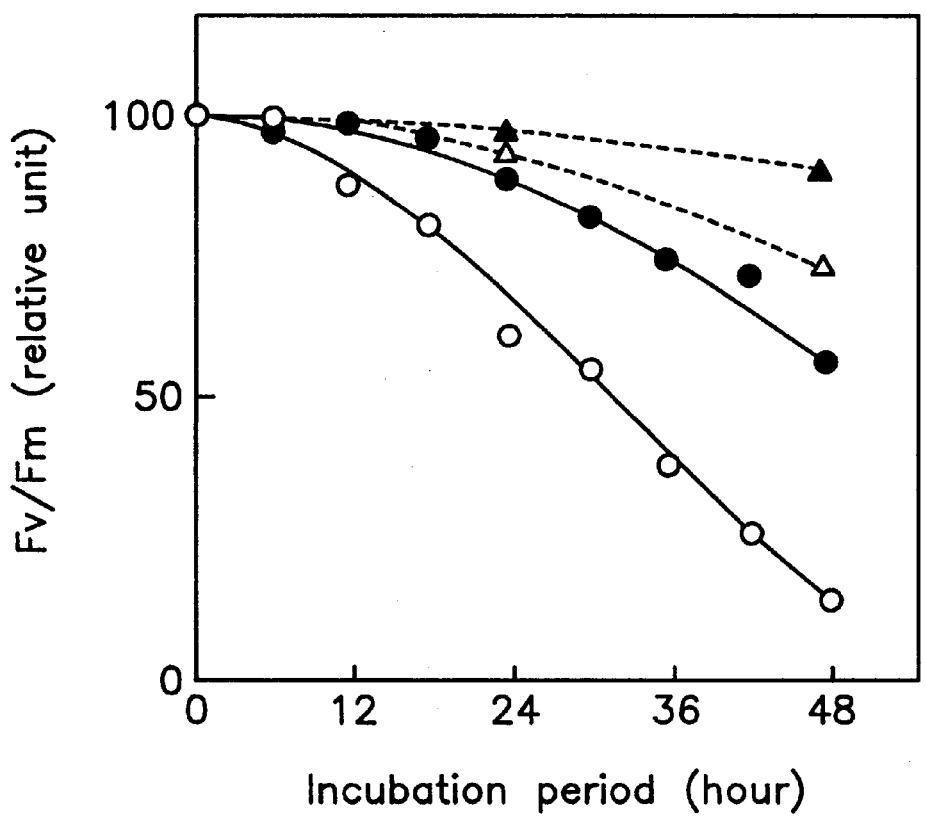
FIG. 14 shows the influence of salt stress on photosynthesis system II in leaves of the wild-type and transformant plants (Arabidopsis). ○: the wild-type plant incubated under light conditions; ●: a transformant plant incubated under light conditions; Δ: the wild-type plant incubated under dark conditions; ▲: a transformant plant incubated under dark conditions. Each data represents the average of triplicate runs with standard deviation of ±5%.

The results are shown in FIG. 14. After incubation for 2 days under light conditions, the wild-type strain almost lost photosynthetic system II activity, while the transformant plants maintained 50% of the original level of photosynthetic system II activity. Under dark conditions, inactivation due to salt stress was much more moderate, but photosynthetic system II activity of the transformant plants was more tolerant than that of the wild-type strain. When the plants were transferred to the medium containing 200 mM sodium chloride, the decrease of photosynthetic system II activity was much more moderate than observed on the medium containing 400 mM sodium chloride, but the transformant plants were again more tolerant to salt stress than the wild-type strain.

Example 13

Preparation of the Chimeric codA Gene Used for Transformation of Rice

Figure 15:
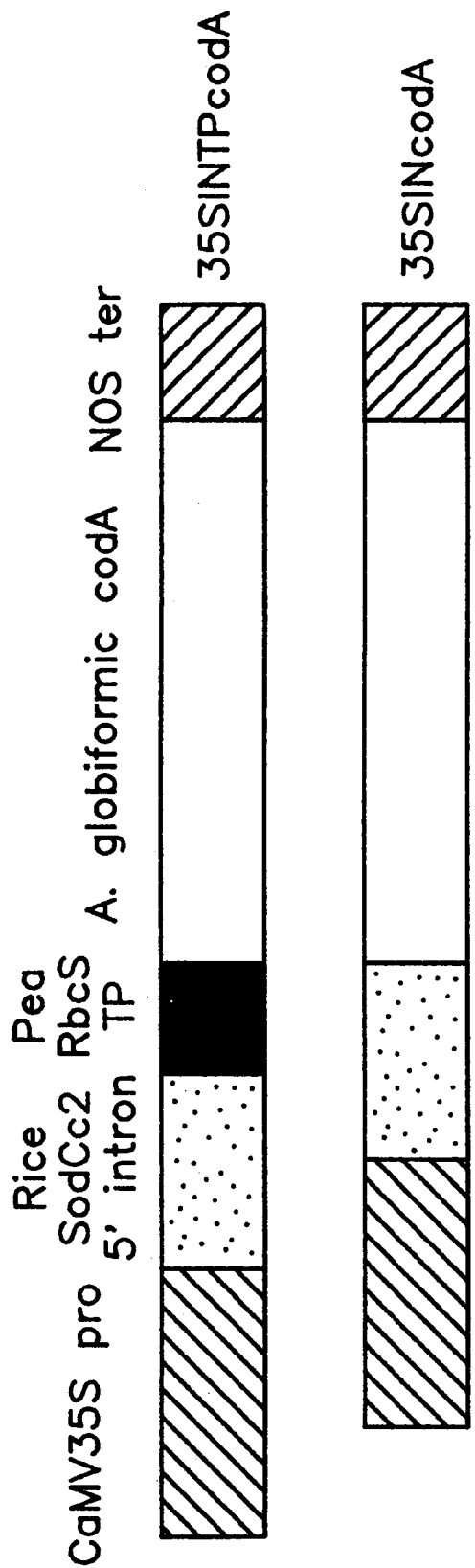
FIG. 15 shows the structures of the two chimeric codA genes used for transformation of rice, i.e. 35SINTPcodA and 35SINcodA.

Two chimeric codA genes (designated as 35SINcodA and 35SINTPcodA, respectively) which are localized on cytosol and plastid, respectively after translation of the choline oxidase gene (codA) from *Arthrobacter globiformis* under transcriptional control of the cauliflower mosaic virus 35S promoter were prepared on the plasmid pUC119 by the procedure described in Example 6 (see FIG. 15). Considering that the presence of an intron is required for high expression of a gene in rice (for example, see Tanaka, A. et al., Nucleic Acids Res. 18:6767–6770, 1990), an intron in the 5' non-translated sequence of the superoxide dismutase gene of rice (SodCc2: Sakamoto, A. et al., FEBS Lett. 358:62–66, 1995) was introduced into the both chimeric genes. Further, a DNA sequence derived from the rbcS transit peptide (Coruzz, G. et al., EMBO J 3:1671–1679, 1984) from pea was added to 35SINTPcodA, in order to transfer the codA protein to the chloroplasts.

Example 14

Transformation of Rice

Each of the two chimeric codA genes prepared in Example 13 was introduced into suspension culture cells from scutellum calli of rice seeds together with the selection marker hygromycin-resistant gene by a particle gun device. The transformed calli were selected based on the antibiotic resistance and redifferentiated into a plant. Polymerase Chain Reaction (PCR) was conducted on the transformed calli or transformed/redifferentiated individuals showing hygromycine resistance, to assess integration and transcription of the codA gene into the nuclear genome by Northern blot technique and select 80 to 100 or more transformants for each codA gene.

Example 15

Analysis of Expression of the codA Gene in Transformant Rice

The transformants obtained in Example 14 were screened by Western blot technique to obtain the transformant rice (the present generation) expressing the codA gene at the protein level, ultimately including 6 individuals carrying the plastid-localized gene and 10 individuals carrying the cytosol-localized gene.

Rice lacks intrinsic choline oxidase activity, but the soluble fractions prepared from leaves or roots of the transformants showed choline oxidase activity. Contrary to expectation, all the individuals of the plastid-type transformants were found to express a lower amount of choline oxidase protein than the cytosol-type, despite the same expression promoter used.

When the expression of the codA gene was further examined by Northern blot technique, any significant difference was not found in the amount of the both genes expressed at the transcription level. When processing of the intron was examined by reverse transcriptive PCR, a plurality of splicing variants containing different 3'-acceptor sites which may not bring about normal translation into protein were detected from the mRNA transcripted from the plastid-type gene. This suggested that the low level protein expression by the plants transformed with the plastid-type gene might be due to abnormal processing of the mRNA precursor. This phenomenon seems to be related to the fact that the sequence encoding the transit peptide used for plastid-targeting of choline oxidase was derived from a dicotyledon (pea rbcS gene). Therefore, it may be readily expected that the expression of the codA in rice chloroplasts would be more efficient and the resultant transformant rice would be more tolerant to salt stress if the sequence encoding the transit peptide was derived from a monocotyledon such as rice rbcS.

Example 16

Betaine Biosynthesis in Transformant Rice

Figure 16A:
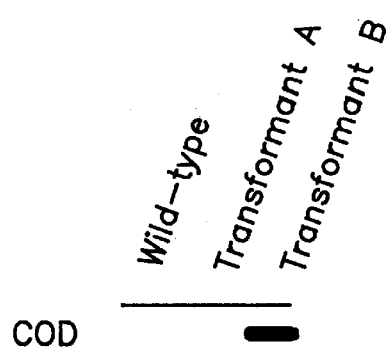
FIG. 16(A-D) shows NMR charts representing betaine accumulation in rice plants of the wild-type strain (FIG. 16B), a transformant (A) (FIG. 16C) not expressing the codA gene, and a transformant (B) (FIG. 16D) expressing the codA gene. In the figure, GB and Ch represent peaks corresponding to betaine and choline, respectively.
Figures 16B, 16C, 16D:
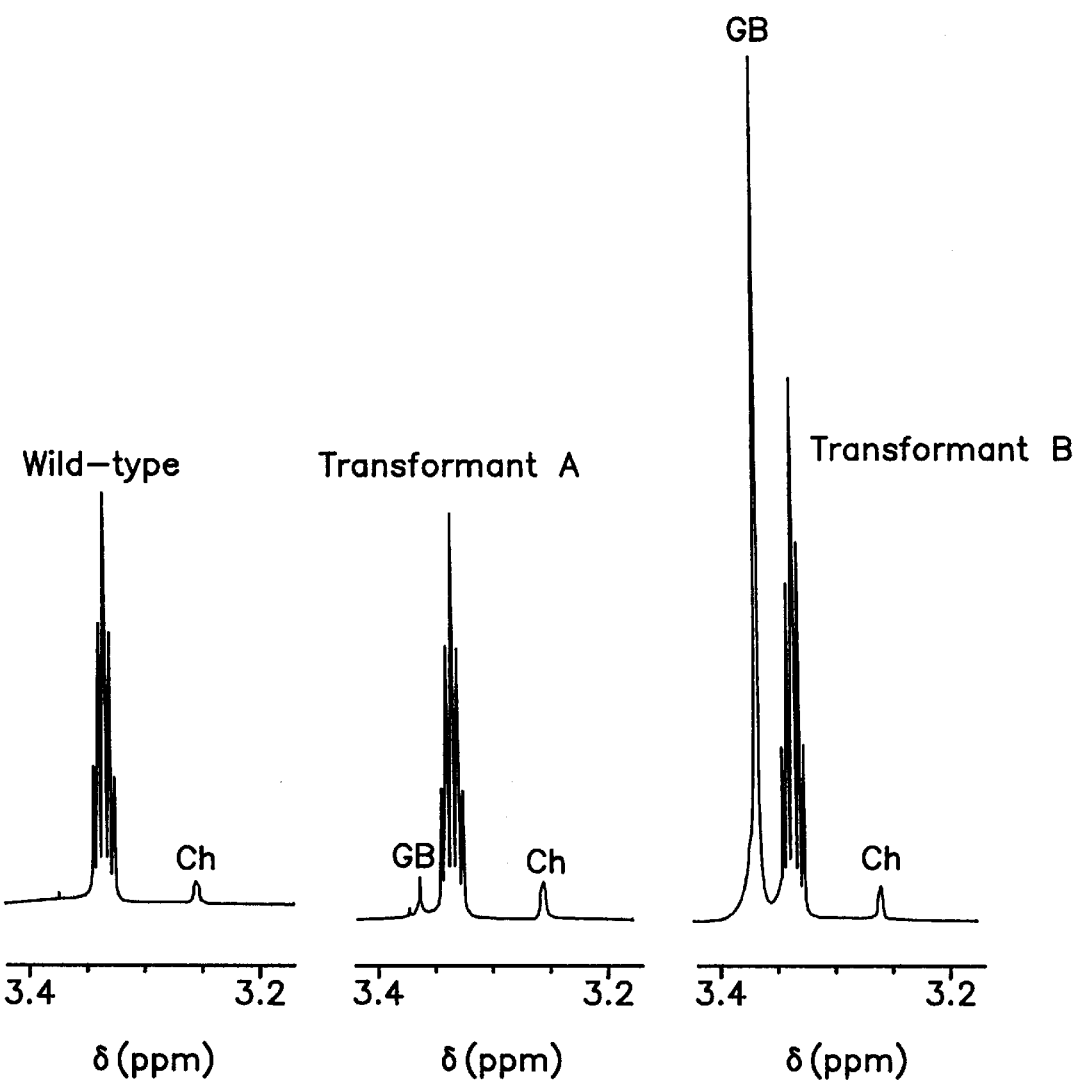

The betaine accumulating in the transformant tissue expressing choline oxidase was detected by proton NMR. FIG. 16 shows the results of the NMR of the wild-type strain, a transformant which does not express the codA gene (FIG. 16A) and a transformant which expresses the codA gene (FIG. 16B).

The transformant which expresses choline oxidase biosynthesized betaine and the amount of betaine accumulation showed a positive correlation with the amount of choline oxidase detected by Western blot technique. Betaine accumulation in leaves was higher than detected in roots and amounted to 4 µmol/g fresh leaf in individuals highly expressing the codA gene. This is the first case in which rice gained the ability to synthesize betaine through a genetic engineering procedure.

Example 17

Evaluation of Salt Tolerance of Transformant Rice

The transformant rice expressing the codA gene grew well equally to the non-transformant (wild-type) under the both of geoponic and hydroponic conditions without showing any apparent abnormality. This indicates that hydrogen peroxide formed as a by-product of betaine biosynthesis was efficiently detoxified in the cells.

Figure 17A:
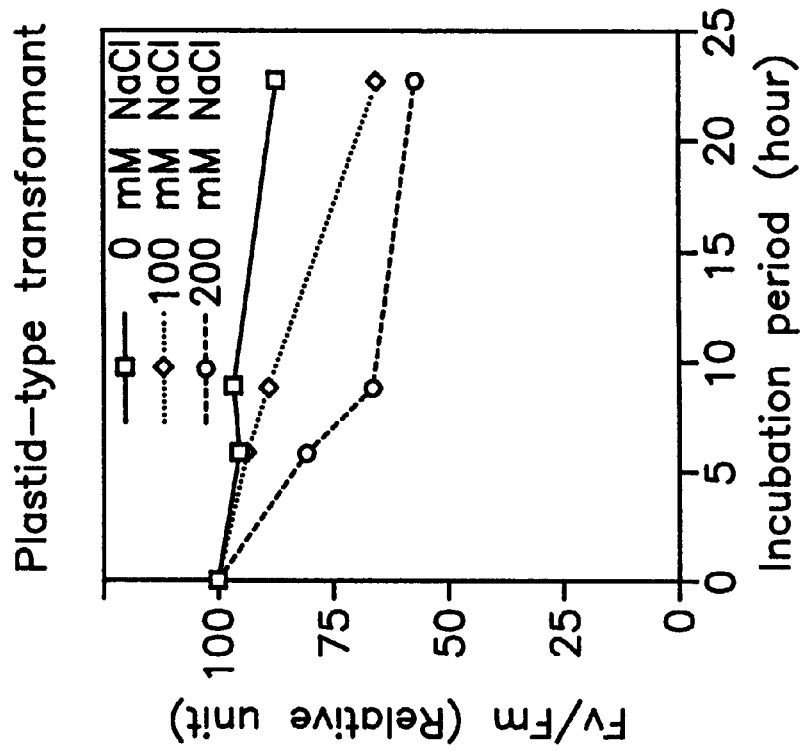
FIG. 17(A-B) shows the influence of salt stress on photosynthetic system II activity of the wild-type (FIG. 17A) and transformant (FIG. 17B) rice plants.
Figure 17B:
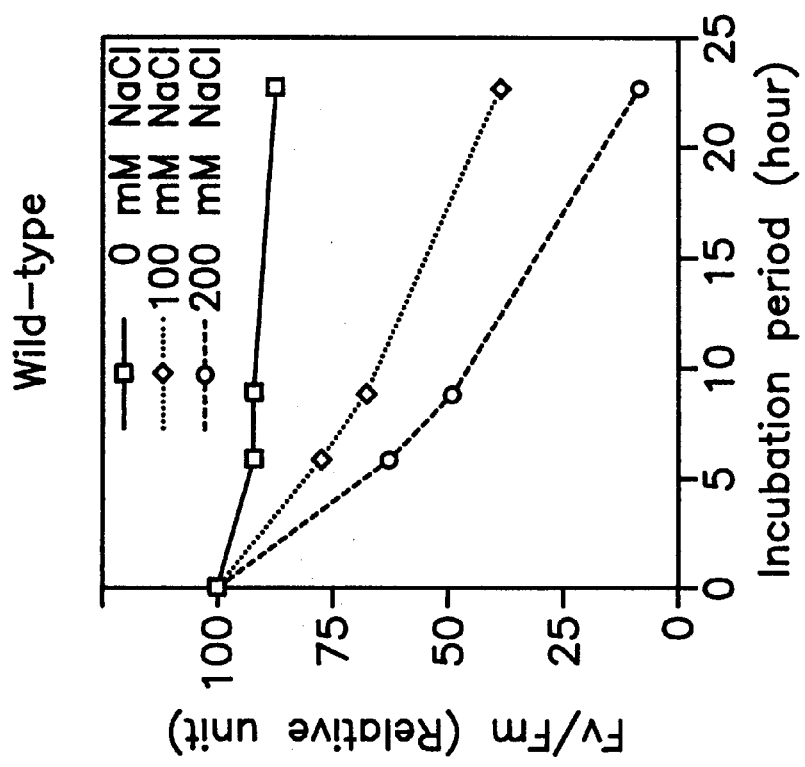

Then, the transformants which could be found to express the codA gene at the level of protein, enzyme activity and betaine production were grown under the hydroponic conditions containing sodium chloride. The influence of Na salt on photosynthetic activity was assessed by chlorophyll fluorescence analysis and compared with the results of the non-transformant (wild-type). When the transformant rice and non-transformant rice were placed in aqueous HYPONEX solutions containing 100 mM and 10 mM sodium chloride and the fluorescence of chlorophyll was determined with time, the transformant was found to retard the inhibition of photosynthetic activity (FIG. 17). Thus, the transformant was found to be more tolerant in salt environment.

What is claimed is:

1. A method for producing a salt-tolerant and/or osmotolerant plant which comprises transforming a plant with a recombinant vector carrying a gene encoding choline oxidase wherein said gene comprises a base sequence encoding the amino acid sequence of SEQ ID NO. 1 or an enzymatically active fragment therefrom.

2. A method according to claim 1 wherein the salt-tolerant and/or osmotolerant plant is a cyanobacterium.

3. A method according to claim 1 wherein the salt-tolerant and/or osmotolerant plant is a higher plant.

4. A method according to claim 3 wherein the higher plant is a dicotyledon.

5. A method according to claim 4 wherein the dicotyledon is a brassicaceous plant.

6. A method according to claim 3 wherein the higher plant is a monocotyledon.

7. A method according to claim 6 wherein the monocotyledon is a gramineous plant.

8. A salt-tolerant and/or osmotolerant plant produced by the method according to claim 1, or a progeny thereof having the same properties.

9. A method for producing a salt-tolerant and/or osmotolerant rice or Arabidopsis plant which comprises transforming a plant with a recombinant vector carrying a gene encoding choline oxidase, wherein said gene comprises a base sequence encoding the amino acid sequence of SEQ ID NO. 1 or an enzymatically active fragment therefrom.

* * * * *

UNITED STATES PATENT AND TRADEMARK OFFICE
CERTIFICATE OF CORRECTION

PATENT NO.    : 6,281,412 B1
DATED         : August 28, 2001
INVENTOR(S)   : Norio Murata It is certified that error appears in the above-identified patent and that said Letters Patent is hereby corrected as shown below:

<u>Title page, Item [54] and Column 1, lines 1-2,</u>
Correct the title of the invention from "METHOD FOR CREATING OSMOTIC-PRESSURE-TOLERANT PLANT" to -- METHOD FOR PRODUCING OSMOTOLERANT PLANTS --.

Signed and Sealed this

Twenty-fifth Day of June, 2002

Attest:

Attesting Officer

JAMES E. ROGAN
*Director of the United States Patent and Trademark Office*